United States Patent

Zinke et al.

[11] Patent Number: 5,969,015
[45] Date of Patent: Oct. 19, 1999

[54] MONOMERIC AND OLIGOMERIC BISPHOSPHITES AS STABILISERS FOR POLYVINYL CHLORIDE

[75] Inventors: Horst Zinke, Reichelsheim/Odw; Karl Josef Kuhn, Lautertal; Wolfgang Wehner, Ober-Ramstadt, all of Germany

[73] Assignee: Witco Vinyl Additives GmbH, Lampertheim, Germany

[21] Appl. No.: 08/929,150

[22] Filed: Sep. 10, 1997

[51] Int. Cl.$^6$ .................... C07F 9/28; C07F 9/02; C08K 5/527; C08K 5/524

[52] U.S. Cl. ............ 524/109; 508/422; 508/423; 524/109; 524/116; 524/117; 524/119; 524/128; 524/151; 524/180; 524/181; 549/220; 558/78; 558/156

[58] Field of Search ................... 524/128, 151, 524/116, 109, 119, 117; 558/156, 78; 549/220; 508/422, 423

[56] References Cited

U.S. PATENT DOCUMENTS

| B 479,556 | 3/1976 | Luders et al. | 260/45.8 |
|---|---|---|---|
| 3,047,608 | 7/1962 | Friedman et al. | 260/461 |
| 3,133,043 | 5/1964 | Rosenfelder et al. | 524/119 |
| 3,205,250 | 9/1965 | Hechenbleikner | 260/461 |
| 3,210,319 | 10/1965 | Huhn et al. | 524/128 |
| 3,283,037 | 11/1966 | Davis | 260/927 |
| 3,342,767 | 9/1967 | Buckley | 260/31.8 |
| 3,592,858 | 7/1971 | Brimer | 260/611.5 |
| 4,312,803 | 1/1982 | Markezich et al. | 260/45.7 |
| 4,348,495 | 9/1982 | Buysch et al. | 524/119 |

FOREIGN PATENT DOCUMENTS

| 0635511 | 1/1995 | European Pat. Off. . |
|---|---|---|
| 0635512 | 1/1995 | European Pat. Off. . |
| 2330979 | 2/1975 | Germany . |
| 3009634 | 9/1980 | Germany . |
| 229995 | 11/1985 | Germany . |
| 52-145452 | 12/1977 | Japan . |
| 53-40719 | 4/1978 | Japan . |
| 53-67755 | 6/1978 | Japan . |
| 55-71744 | 5/1980 | Japan . |
| 57-65743 | 4/1982 | Japan . |
| 61-209250 | 9/1986 | Japan ..................... 524/128 |

OTHER PUBLICATIONS

Derwent Abst. 37492A/21 for JP 53040719.
Derwent Abst. 49019C/28 for JP 55071744.
Derwent Abst. 54058A/30 for JP 53067755.
Derwent Abst. 44420 E/22 for JP 57065743 & Chem Abst. 97(20):164031q.
Derwent Abst. 05623A/03 for JP 52145452.
Abstract for DD 229995.
Chem. Abst. 125:33956.
Chem. Abst. 59:12800q.
Chem. Abst. 63:5840e.

*Primary Examiner*—Veronica P. Hoke
*Attorney, Agent, or Firm*—Scully, Scott, Murphy & Presser

[57] ABSTRACT

Compositions, comprising
(i) a halogen-containing polymer material, and
(ii) at least one phosphite of formula I

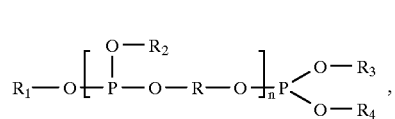

wherein
n is a number from 1 to 6,
R is a divalent linking group of formulae as defined herein as well as of novel compounds of formula I and their use as stabilisers.

43 Claims, No Drawings

MONOMERIC AND OLIGOMERIC BISPHOSPHITES AS STABILISERS FOR POLYVINYL CHLORIDE

The present invention relates to compositions comprising a halogen-containing polymeric material, in particular a vinyl chlorid homo- or copolymer, and at least one monomeric or oligomeric organic bisphosphite, to the use of the latter for stabilising said polymeric material against, in particular, oxidative, thermal and/or light-induced degradation; as well as to novel monomeric and oligomeric bisphosphites, to compositions comprising these and to the use thereof for stabilising polymers and lubricants.

Bisphosphites, which are derived from divalent alcohols, are known in great number from the literature, inter alia from: U.S. Pat. No. 3,047,608, U.S. Pat. No. 3,342,767, U.S. Pat. No. 3,205,250, U.S. Pat. No. 3,283,037, U.S. Pat. No. 3,592,858, EP-A-635512, EP-A-63551 1, DE-A-3009634, DE-A-2330979, DD-A-229995, JP-A-52-145452, JP-A-57-65743, JP-A-53-67755, JP-A-55-71744 and JP-A-53-40719. Phosphites are known in general as processing stabilisers for polyolefins, elastomers, polyvinyl choride and other polymers and are of substantial practical importance. The patent publications cited above therefore also describe the cited bisphosphites as stabilisers for a series of polymer substrates and some of them also as stabilisers for polyvinyl choride (PVC).

Owing to the increased demands are made on the effectivity and environmental compatibility of stabilisers, there continues to be a need for finding and optimising stabilisers and stabiliser systems, also in the field of the organic phosphites.

It has been found that a very specific group of bisphosphites is particularly suitable as stabilisers or costabilisers for, in particular, halogen-containing polymers, such as PVC.

Accordingly, this invention relates to a composition, comprising (i) a halogen-containing polymeric material, and
(ii) at least one phosphite of formula I

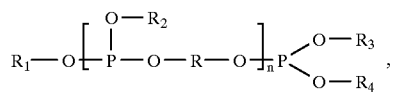
(I)

wherein
n is a number from 1 to 6,
R is a divalent linking group of formulae

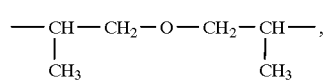
(BR1)

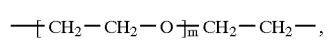
(BR2)

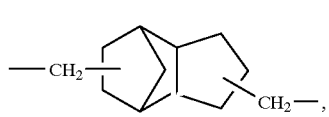
(BR3)

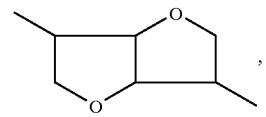
(BR4)

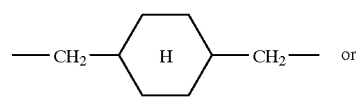
or (BR5)

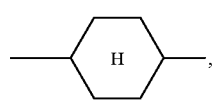
(BR6)

m is a number from 1 to 5, $R_1$, $R_2$, $R_3$ and $R_4$ are each independently of one another $C_4$–$C_{22}$alkyl, $C_7$–$C_9$phenylalkyl, $C_5$–$C_8$cycloalkyl or $C_1$–$C_4$alkyl-$C_5$–$C_8$cycloalkyl, or $R_1$ and $R_2$ and/or $R_3$ and $R_4$ together are $C_2$–$C_9$alkylene or a group of formula

with the provisos that a) the composition does not contain any Ba-, Zn- and/or Ca-stabilisers if $R_1$+$R_2$ and $R_3$+$R_4$ are a group of formula

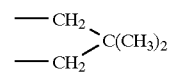

and if R is BR1 or BR2, and b) m is different from 2, if $R_1$, $R_2$, $R_3$ and $R_4$ are identical and are $C_{12}$–$C_{22}$alkyl and if R is BR2.

Alkyl radicals and alkylene radicals, such as those occurring in the general substituent definitions, can be unbranched or branched. Typical examples are methyl, ethyl, propyl, isopropyl, butyl, isobutyl, tert-butyl, pentyl, hexyl, heptyl, octyl, isooctyl, 2-ethylhexyl, nonyl, decyl, undecyl, dodecyl, tridecyl, hexadecyl, octadecyl, eicosyl and heneicosyl. Typical examples of alkylene groups ($R_1$+$R_2$, $R_3$+$R_4$) are ethylene, propylene, 2-methylpropylene, 2,2-dimethylpropylene, 2-methyl-2-n-propyl-propylene and 2-ethyl-2-n-butyl-propylene. A six-membered ring is preferably formed with the

group.

Unsubstituted or $C_1$–$C_4$alkyl-substituted $C_5$–$C_8$cycloalkyl is typically cyclopentyl, methylcyclopentyl, dimethylcyclopentyl, cyclohexyl, methylcyclohexyl, dimethylcyclohexyl, trimethylcyclohexyl, tert-butylcyclohexyl, cycloheptyl or cyclooctyl. Cyclohexyl, methylcyclohexyl and dimethylcyclohexyl are preferred.

$C_7$–$C_9$Phenylalkyl is typically benzyl, phenethyl, α-methylbenzyl or α,α-dimethylbenzyl.

Component (i) is preferably a chlorine-containing polymer, in particular a vinyl chloride homo- or copolymer, e.g. polyvinyl chloride.

In formula I, n is preferably a number from 1 to 5, more preferably from 1 to 4, typically from 1 to 3, most preferably 1.

Preferred compositions according to this invention comprise compounds of formula I, wherein $R_1$, $R_2$, $R_3$ and $R_4$ are each independently of one another $C_6$–$C_{22}$alkyl or $C_7$–$C_9$phenylalkyl, or $R_1$ and $R_2$ and/or $R_3$ and $R_4$ together are $C_2$–$C_9$alkylene, preferably those compounds of formula I, wherein m is 1 or 2, and $R_1$, $R_2$, $R_3$ and $R_4$ are each independently of one another $C_6$–$C_{15}$-alkyl, $C_7$–$C_9$phenylalkyl, or $R_1$ and $R_2$ and/or $R_3$ and $R_4$ together are $C_2$–$C_9$alkylene.

Preferred linking groups R in formula I are those of formulae BR1, BR3 and BR4 or of formulae BR1, BR2 and BR3, preferably those of formula BR1. In the latter case, $R_1$, $R_2$, $R_3$ and $R_4$ are each independently of one another conveniently $C_6$–$C_{15}$alkyl or $C_7$–$C_8$phenylalkyl, preferably $C_8$–$C_{11}$alkyl.

Compounds of formula I which are of particular practical interest are those, wherein $R_1$, $R_2$, $R_3$ and $R_4$ or $R_1$+$R_2$ and $R_3$+$R_4$ are identical.

Where R in compounds of formula I is the linking group of formula BR1, $R_1$, $R_2$, $R_3$ and $R_4$ are preferably $C_6$–$C_{11}$alkyl, $C_7$–$C_8$phenylalkyl or $C_5$–$C_8$cycloalkyl, or $R_1$ and $R_2$ and/or $R_3$ and $R_4$ together are $C_2$–$C_9$alkylene.

Particularly interesting novel compositions are in general those, which comprise compounds of formula I enthalten, wherein $R_1$, $R_2$, $R_3$ and $R_4$ are $C_6$–$C_{22}$alkyl, $C_7$–$C_9$phenylalkyl or $C_5$–$C_8$cycloalkyl.

The compounds of formula I are excellent stabilisers for halogen-containing polymeric materials and are particularly suitable for stabilising them against the adverse influence of heat, oxygen and/or light, in particular UV light. Accordingly, the act as thermostabilisers, antioxidants and light stabilisers. To be mentioned in particular is their thermostabilising action which permits processing the cited polymers with as little damage as possible in customary manner.

The novel compositions generally comprise conveniently from 0.005 to 10, in particular from 0.01 to 10, preferably from 0.01 to 5, typically from 0.05 to 3, most preferably from 0.05 to 2% by weight, of compounds of formula I, based on the polymer to be stabilised.

Halogen-containing, in particular chlorine-containing, polymeric materials (component (i)) can be for example: polymers of vinyl chloride, vinyl resins containing vinyl chloride units in their structure, such as copolymers of vinyl chloride and vinyl esters of aliphatic acids, preferably vinyl acetate, copolymers of vinyl chloride with esters of the acrylic and methacrylic acid and with acrylonitrile, copolymers of vinyl chloride with diene compounds and unsaturated dicarboxylic acids or their anhydrides, such as copolymers of vinyl chloride with diethylmaleate, diethylfumarate or maleic acid anhydride, postchlorinated polymers and copolymers of vinyl chloride, copolymers of vinyl chloride and vinylidene chloride with unsaturated aldehydes, ketones and others, such as acrolein, crotonaldehyde, vinyl methyl ketone, vinyl methyl ether, vinyl isobutyl ether and similar compounds; polymers of vinylidene chloride and copolymers thereof with vinyl chloride and other polymerisable compounds; polymers of vinyl chloroacetate and dichlorodivinyl ether; chlorinated polymers of vinyl acetate, chlorinated polymeric esters of acrylic acid and of alpha-substituted acrylic acid; polymers of chlorinated styrenes, typically dichlorostyrene; chlorinated rubbers; chlorinated polymers of ethylene; polymers and postchlorinated polymers of chlorobutadiene and their copolymers with vinyl chloride; as well as mixtures of the cited polymers with themselves or with other polymerisable compounds.

Other examples are graft polymers of PVC with EVA, ABS and MBS. Preferred substrates are also mixtures of the above-mentioned homo- and copolymers, preferably vinyl chloride homopolymers, with other thermoplastic or/and elastomeric polymers, preferably blends with ABS, MBS, NBR, SAN, EVA, CPE, MBAS, PMA, PMMA, EPDM and polyactones.

Chlorine-containing polymers are particularly preferably polyvinyl chloride, in particular as suspension polymers, bulk polymers and emulsion polymers.

Within the scope of this invention, component (i) is also to be understood in particular as recyclates of chlorine-containing polymers, i.e. the polymers described in more detail hereinabove, which have been damaged by processing, use or storage. PVC recyclate is particularly preferred. The recyclates can also contain minor amounts of foreign matter, such as paper, pigments and adhesives, which are often difficult to remove. These foreign materials can also originate from the contact with diverse substances during use or processing, such as fuel residues, paint components, traces of metal, initiator residues or also traces of water.

The novel compositions usually contain further customary additives, typically as component (iii) lubricants, plasticisers, pigments, antiblocking agents, modifiers, processing assistants, blowing agents, antistatic agents, biocides, antifogging agents, colourants, flame retardants, fillers, antioxidants, light stabilisers and/or other processing stabilisers.

Additional components (iii) to be mentioned are additives from the groups of the organic or inorganic zinc, alkali metal, alkaline earth metal or/and aluminium compounds, of the sterically hindered amines, of other organic amines, of the organotin or/and organoantimony compounds, of the polyols, epoxides, hydrotalcites, zeolites, dawsonites, 1,3-diketones, 3-ketocarboxylates or/and perchlorates.

Some groups of additives which are suitable as component (iii) alone or in combination are exemplified below:

a) Zinc Compounds and other Metal Compounds

The organic zinc compounds, which preferably contain a Zn-O-bond, are typically zinc enolates, zinc phenolates or/and zinc carboxylates. These latter are compounds from the series of the aliphatic saturated and unsaturated $C_{1-22}$carboxylates, of the aliphatic saturated or unsaturated $C_{2-22}$carboxylates, which are substituted by at least one OH group or/and whose chain is interrupted by at least one or more than one O atom (oxa acids), of the cyclic and bicyclic carboxylates containing 5–22 carbon atoms, of the phenylcarboxylates which are unsubstituted or substituted by at least one OH group and/or by $C_{1-16}$alkyl, of the phenyl-$C_{1-16}$alkylcarboxylates, or of the unsubstituted or $C_{1-12}$alkyl-substituted phenolates, or of abietic acid. Zn-S compounds are typically zinc mercaptides, zinc mercaptocarboxylates and zinc mercaptocarboxylates.

Examples to be mentioned the zinc salts of the monovalent carboxylic acids, such as acetic acid, propionic acid, butyric acid, valeric acid, hexanoic acid, oenanthic acid, octanoic acid, neodecanic acid, 2-ethylhexanoic acid, pelargonic acid, decanoic acid, undecanoic acid, dodecanoic acid, tridecanoic acid, myristylic acid, palmitic acid, lauric acid, isostearic acid, stearic acid, 1,2-hydroxystearic acid, 9,10-dihydroxystearic acid, oleic acid, ricinolic acid, 3,6-dioxaheptanoic acid, 3,6,9-trioxadecanoic acid, behenic acid, benzoic acid, p-tert-butylbenzoic acid, dimethylhydroxybenzoic acid, 3,5-di-tert-butyl-4-hydroxybenzoic acid, tolylic acid, dimethylbenzoic acid, ethylbenzoic acid, n-proylbenzoic acid, salicylic acid, p-tertoctylsalicylic acid, and sorbic acid, cinnamic acid, mandelic acid, glycolic acid; zinc salts of the divalent carboxylic acids or of the monoesters, typically oxalic acid, malonic acid, succinic acid, glutaric acid, adipic acid, fumaric acid, pentane-1,5-dicarboxylic acid, hexane-1,6-dicarboxylic acid, heptane-1,7-dicarboxylic acid, octane-1,8-dicarboxylic acid, 3,6,9-trioxadecane-1,10-dicarboxylic acid, lactic acid, malonic acid, maleic acid, tartaric acid, malic acid, salicylic acid, polyglycol dicarboxylic acid (n=10-12), phthalic acid, isophthalic-acid terephthalic acid and hydroxyphthalic acid; and of the di- or triesters of the tri-or tetravalent carboxylic acids, typically hemimellitic acid, trimellitic acid, pyromellitic acid, citric acid and also so-called overbased zinc carboxylates or zinc laurylmercaptide, zinc thioglycolate, zinc thiosalicylate, zinc-bis-i-octylthioglycolate, zinc mercaptopropionate, zinc thiolactate, zinc thiomalate, zinc-bis-octylmercaptopropionate, zinc-bis-isooctylthiolactate and zinc-bis-laurylthiomalate.

The zinc enolates are preferably enolates of acetylacetone, benzoylacetone, dibenzoylmethane as well as enolates of acetoacetic acid and benzoyl acetate and also dehydracetic acid. It is also possible to use inorganic zinc compounds, such as zinc oxide, zinc hydroxide, zinc carbonate, basic zinc carbonate or zinc sulfide.

It is preferred to use neutral or basic zinc carboxylates of a carboxylic acid having 1 to 22 carbon atoms (zinc soaps), typically benzoates or alkanoates, preferably $C_8$alkanoates, stearate, oleate, laurate, palmitate, behenate, versatate, hydroxystearates and hydroxyoleates, ricinoleate, dihydroxystearates, p-tert-butylbenzoate, or (iso)octanoate. Stearate, oleate, versatate, benzoate, p-tert-butylbenzoate and 2-ethylhexanoate are particularly preferred.

In addition to the cited zinc compounds, it is also possible to use organic aluminium compounds, magnesium compounds, calcium compounds, barium compounds, potassium compounds or sodium compounds, the anionic radicals corresponding to the groups listed for the zinc compounds. The preferred compounds of this kind include aluminium carboxylate, calcium carboxylate, barium carboxylate, potassium carboxylate or magnesium carboxylate, such as basic aluminium monostearate, basic aluminium distearate, aluminium tristearate, calcium stearate, aluminium octoate, aluminium-2-ethylhexanoate, calcium-2-ethylhexanoate, barium-2-ethylhexanoate, potassium-2-ethylhexanoate, aluminium laurate, calcium oleate, barium oleate, calcium-t-butylbenzoate, basic aluminium acetates as well as aluminium enolates or magnesium enolates, such as aluminium acetylacetonate, magnesium acetylacetonate and also aluminium alcoholates or magnesium alcoholates as well as the corresponding barium compounds. Also to be mentioned here are oxides, hydroxides, carbonates and basic carbonates of the above-cited metals as well as their mixed salts with organic acids. Typical examples are NaOH, KOH, CaO, $Ca(OH_2)$, MgO, $Mg(OH)_2$, $CaCO_3$, $MgCO_3$ dolomite, huntite, as well as fatty acid Na-, K-, Ca or Mg-salts. In the case of alkaline earth metal carboxylates and zinc carboxylates it is also possible to use adducts thereof with MO or $M(OH)_2$ (M=Ca, Mg, Ba, Sr or Zn), so-called overbased compounds.

The described metal compounds or mixtures thereof can be used in amounts of e.g. 0.0001 to 10, conveniently of 0.001 to 5, preferably of 0.01 to 3, e.g. of 0.01 to 1, parts by weight, based on 100 parts of halogen-containing polymer. They can also be obtained as mixed salts (coprecipitates).

b) Other phosphites

Typical examples are trioctyl-, tridecyl-, tridodecyl-, tritridecyl-, tripentadecyl-, trioleyl-, tristearyl-, triphenyl-, tricresyl-, trisnonylphenyl-, tris-2,4-t-butylphenyl- or tricyclohexylphosphite.

Other suitable phosphites are differently mixed aryldialkyl- or alkyldiarylphosphites, such as phenyldioctyl-, phenyldidecyl-, phenyldidodecyl-, phenylditridecyl-, phenylditetradecyl-, phenyldipentadecyl-, octyldiphenyl-, decyldiphenyl-, undecyldiphenyl-, dodecyldiphenyl-, tridecyldiphenyl-, tetradecyldiphenyl-, pentadecyldiphenyl-, oleyldiphenyl-, stearyldiphenyl- and dodecyl-bis-2,4-di-t-butylphenylphosphite.

Phosphites of different diols or polyols can also be advantageously used: typically tetraphenyldipropylene glycol diphosphite, polydipropylene glycol phenyl phosphite, tetramethylolcyclohexanoldecyl diphosphite, tetramethylolcyclohexanolbutoxyethoxyethyl diphosphite, tetramethylolcyclohexanolnonylphenyl diphosphite, bisnonylphenyl-di-trimethylolpropane diphosphite, bis-2-butoxyethyl-di-trimethylolpropane diphosphite, trishydroxyethylisocyanurate hexadecyl triphosphite, didecylpentaerythritol diphosphite, distearylpentaerythritol diphosphite, bis-2,4-di-t-butylphenylpentaerythritol diphosphite, as well as mixtures of these phosphites and aryl/alkylphosphite mixtures of the random composition

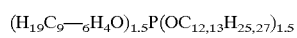

or

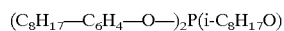

or

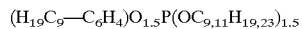

The organic phosphites can be used in an amount of e.g. 0.01 to 10, conveniently of 0.05 to 5 and, preferably, of 0.1 to 3, parts by weight, based on 100 parts by weight of component (i).

c) Polyols

Suitable compounds of this type are for example: pentaerythritol, dipentaerythritol, tripentaerythritol, bistrimethylolpropane, trimethylolethane, bistrimethylolethane, trimethylolpropane, bis-trimethylolpropane, sorbitol, maltite, isomaltite, lactite, lycasine, mannitol, xylite, inosite, lactose, leucrose, tris (hydroxyethyl)isocyanurate, palatinite, tetramethylolcyclohexanol (TMCH), tetramethylolcyclopentanol, tetramethylolcyclopyranol, glycerol, diglycerol, polyglycerol, thiodiglycerol, or 1-0-α-D-glycopyranosyl-D-mannitol dihydrate as well as polyvinyl alcohol and cyclodextrins; and also condensates of such polyols, typically dipentaerythritol adipate, glycerol oleate, glycerol trioleate, and the like. TMCH, pentaerythritol, dipentaerythritol, sorbitol and the disaccharide alcohols are preferred.

The polyols can be used in an amount of e.g. 0.01 to 20, conveniently of 0.1 to 20 and, preferably, of 0.1 to 10, parts by weight, based on 100 parts by weight of component (i).

d) 1,3-Dicarbonyl Compounds

Illustrative examples of 1,3-dicarbonyl compounds are acetylacetone, butanoylacetone, heptanoylacetone, stearoylacetone, palmitoylacetone, lauroylacetone, 7-tert-nonylthioheptane-2,4-dione, benzoylacetone, dibenzoylmethane, lauroylbenzoylmethane, palmitoylbenzoylmethane, stearoylbenzoylmethane, isooctylbenzoylmethane, 5-hydroxycapronylbenzoylmethane, tribenzoylmethane, bis(4-methylbenzoyl)methane, benzoyl-p-chlorobenzolylmethane, bis(2-hydroxybenzoyl)methane, 4-methoxybenzoylbenzoylmethane, bis(4-methoxybenzoyl)methane, 1-benzoyl-1-acetylnonane, benzoylacetylphenylmethane, stearoyl-4-methoxybenzoylmethane, bis(4-tert-butylbenzoyl)methane, benzoyl-formylmethane, benzoylphenylacetylmethane, bis(cyclohexanoyl)methane, di(pivaloyl)methane, methyl acetoacetate, ethyl acetoacetate, hexyl acetoacetate, octyl acetoacetate, dodecyl acetoacetate or octadecyl acetoacetate, ethyl benzoylacetate, butyl benzoylacetate, 2-ethylhexyl benzoylacetate, dodecyl benzoylacetate or octadecyl benzoylacetate, ethyl stearoylacetate, propyl stearoylacetate, butyl stearoylacetate, hexyl stearoylacetate or octyl stearoylacetate and dehydracetoactic acid as well as the zinc, alkali metal, alkaline earth metal or aluminium salts thereof.

The 1,3-dicarbonyl compounds can be used in an amount of e.g. 0.01 to 10, conveniently of 0.01 to 3 and, preferably, of 0.01 to 2, parts by weight, based on 100 parts by weight of PVC.

e) Thiophosphites and Thiophosphates

Thiophosphites or thiophosphates are to be understood as compounds of the general type $(RS)_3P$, $(RS)_3P=O$ or $(RS)_3P=S$, such as those described in DE-A-2809492, EP-A-090770 and EP-A-573394. Typical examples are: trithiohexylphosphite, trithiooctylphosphite, trithiolaurylphosphite, trithiobenzylphosphite, trithiophosphorous acid-tris-[carboxy-i-octyloxy]methyl ester, trithiophosphoric acid-S,S,S-tris-[carbo-i-octyloxy]methyl ester, trithiophosphoric acid-S,S,S-tris-[carbo-2-ethylhexyloxy]methyl ester, trithiophosphoric acid-S,S,S,-tris-1-[carbohexyloxy]ethyl ester, trithiophosphoric acid-S,S,S-tris-1-[carbo-2-ethylhexyloxy]ethyl ester, trithiophosphoric acid-S,S,S-tris-2-[carbo-2-ethylhexyloxy]ethyl ester. The thiophosphites or thiophosphates can conveniently be present in an amount of 0.01 to 20% by weight, preferably of 0.1 to 5% by weight, more preferably of 0.1 to 1% by weight, in the halogen-containing polymer.

f) Mercaptocarboxylate

Illustrative examples of these compounds are: esters of thioglycolic acid, thiomalic acid, mercaptopropionic acid, of mercaptobenzoic acids or of thiolactic acid, such as described, inter alia, in FR-A-2459816, EP-A-90748, FR-A-2552440 and EP-A-365483. The mercaptocarboxylates also include corresponding polyesters or their partial esters.

They can conveniently be present in an amount of 0.01 to 10% by weight, preferably of 0.1 to 5% by weight, more preferably of 0.1 to 1% by weight, in the halogen-containing polymer.

g) Epoxides and Epoxidised Fatty Acid Esters

In this connection, epoxidised esters of fatty acids from natural sources, such as soy bean oil or rape seed oil, are to be mentioned in particular.

The epoxy compounds are preferably used in amounts of e.g. 0.1 part by weight, based on 100 parts by weight of composition, conveniently of 0.1 to 30, preferably of 0.5 to 25 parts by weight, based on 100 parts by weight of component (i). Other examples are epoxidised polybutadiene, epoxidised linseed oil, epoxidised fish oil, epoxidised tallow, methylbutyl- or 2-ethylhexylepoxystearate, tris(epoxypropyl)isocyanurate, epoxidised castor oil, epoxidised sunflower oil, 3-phenoxy-1,2-epoxypropane, diglycidyl ether of bisphenol A, vinyl-cyclohexene diepoxide, dicyclopentadiene diepoxide and 3,4-epoxycyclohexylmethyl-3,4-epoxycyclohexanecarboxylate.

Suitable epoxides are also derivatives of bisphenol A and bisphenol F, as described, inter alia, in U.S. Pat. No. 5,492,949, U.S. Pat. No. 5,519,077 and U.S. Pat. No. 5,543,449.

g) Dihydropyridines and Polydihydropyridines

Suitable monomeric dihydropyridines are the compounds described, inter alia, in FR-A-2039496, EP-A-2007, EP-A-362012, EP-A-24754 and EP-A-716123. Preferred compounds are those of formula

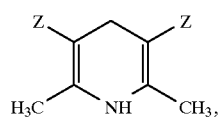

wherein Z is $CO_2CH_3$, $CO_2C_2H_5$, $CO_2{}^nC_{12}H_{25}$ or $-CO_2C_2H_4-S-{}^nC_{12}H_{25}$.

Polydihydropyridines are preferably compounds of the following formula

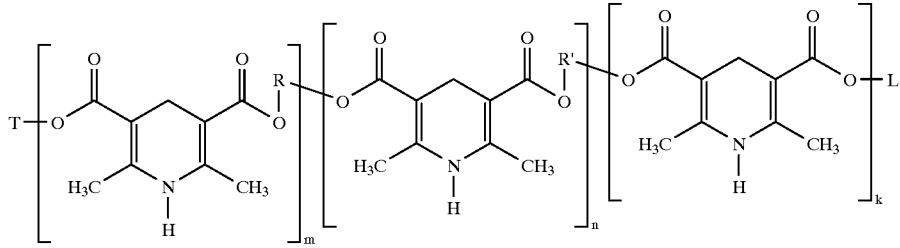

wherein

T is unsubstituted $C_{1-2}$alkyl.

L has the same meaning as T.

m and n are numbers from 0 to 20, k is 0 or 1,

R and R' are each independently of the other ethylene, propylene, butylene or an alkylene- or cycloalkylenebismethylene group of the $-(-C_pH_{2p}-X-)_tC_pH_{2p}$ type.

p is 2 to 8, t is 0 to 10,

X is oxygen or sulfur.

Such compounds are described in more detail in EP-A-286887. The (poly-)dihydropyridines can be used in the halogen-containing polymer conveniently in an amount of 0.001 to 5 and, preferably, of 0.005 to 1, parts by weight, based on 100 parts of the polymer. Thiodiethylene-bis[5- methoxycarbonyl-2,6-dimethyl-1,4-dihydropyridine-3-carboxylate] and 1,4-dihydro-2,6-dimethyl-3,5-dicarbododecyloxypyridine are particularly preferred.

h) Perchlorates

Typical examples are those of formula $M(ClO_4)_n$, wherein M is Li, Na, K, Mg, Ca, Ba, Zn, Al, Ce or La. Depending on the valency of M, the index n is 1, 2 or 3. The perchlorates can be complexed with alcohols or ether alcohols. Each perchlorate can be used in different standard forms of presentation; e.g. as salt or aqueous solution of the salts or of the free acid applied to a substrate such as PVC, calcium silicate, zeolites or hydrotalcites, or can be obtained by chemical reaction of hydrotalcite with perchloric acid.

The perchlorates can be used in an amount of e.g. 0.001 to 5, conveniently of 0.01 to 3, particularly preferably of 0.01 to 2, parts by weight, based on 100 parts by weight of component (i).

i) Hydrotalcites and Zeolites

The chemical composition of these compounds is known to the skilled person, e.g. from DE-A-3843581, U.S. Pat. No. 4,000,100, EP-A-062813, WO-A-93/20135.

Compounds of the hydrotalcite series can be described by the general formula III

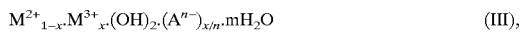

wherein $M^{2+}$=one or more of the metals selected from the group consisting of Mg, Ca, Sr, Zn and Sn, $M^{3+}$=Al or B, $A^n$ is an anion of valency n, n is a number from 1 to 2, $0 < x \leq 0.5$, m is a number from 0 to 20.

$A^n$=$OH^-$, $ClO_4^-$, $HCO_3^-$, $CH_3COO^-$, $C_6H_5COO^-$, $CO_3^{2-}$, $SO_4^{--}$,

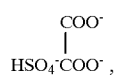

$(CHOHCOO)_2^{2-}$, $(CH_2COO)_2^{2-}$, $CH_3CHOHCOO^-$, $HPO_3^{2-}$ or $HPO_4^{2-}$ is preferred.

It is also possible to use hydrotalcites comprising LiOH or $Li_2CO_3$ ("solid solution").

Examples of hydrotalcites are $Al_2O_3 \cdot 6MgO \cdot CO_2 \cdot 12H_2O$, $Mg4.5Al_2(OH)_{13} \cdot CO_3 \cdot 3.5H_2O$, $4MgO \cdot Al_2O_3 \cdot CO_2 \cdot 9H_2O$, $4MgO \cdot Al_2O_3 \cdot CO_2 \cdot 6H_2O$, $ZnO \cdot 3MgO \cdot Al_2O_3 \cdot CO_2 \cdot 8-9H_2O$ and $ZnO \cdot 3MgO \cdot Al_2O_3 \cdot CO_2 \cdot 5-6H_2O$. Compounds of the zeolite series (alkali metal alumosilicates or alkaline earth metal alumosilicates) can be described by the general formula (IV)

wherein n is the charge of cation M;

M is an element of the first or second main group of the Periodic Table, such as Li, Na, K, Mg, Ca, Sr or Ba, or Zn, y:x is a number from 0.8 to 15, preferably from 0.8 to 1.2; and w is a number from 0 to 300, preferably from 0.5 to 30.

Structures may be found, for example, in "Atlas of Zeolite" by W. M. Meier and D. H. Olson, Butterworth-Heinemann, 3. Ed. 1992.

Examples of zeolites are sodium alumosilicates of formulae $Na_{12}Al_{12}Si_{12}O_{48} \cdot 27 H_2O$ [zeolite A], $Na_6Al_6Si_6O_{24} \cdot 2 NaX \cdot 7.5 H_2O$, X=OH, halogen, $ClO_4$ [sodalite]; $Na_6Al_6Si_{30}O_{72} \cdot 24 H_2O$; $Na_8Al_8Si_{40}O_{96} \cdot 24 H_2O$; $Na_{16}Al_{16}Si_{24}O_{80} \cdot 16 H_2O$; $Na_{16}Al_{16}Si_{32}O_{96} \cdot 16 H_2O$; $Na_{56}Al_{56}Si_{136}O_{384} \cdot 250 H_2O$ [zeolite Y], $Na_{86}Al_{86}Si_{106}O_{384} \cdot 264 H_2O$ [zeolite X]; as well as X- and Y-zeolite in an Al/Si ratio of 1/1; or the zeolites which may be represented by the partial or complete exchange of the sodium atoms by Li atoms, K atoms, Mg atoms, Ca atoms, Sr atoms or Zn atoms such as $(Na,K)_{10}Al_{10}Si_{22}O_{64} \cdot 20 H_2O$; $Ca_{4.5}Na_3[(AlO_2)_{12}(SiO_2)_{12}] \cdot 30 H_2O$; $K_9Na_3[(AlO_2)_{12}(SiO_2)_{12}] \cdot 27 H_2O$.

Other suitable zeolites are: $Na_2O \cdot Al_2O_3 \cdot (2$ to $5)$ $SiO_2 \cdot (3.5$ to $10)$ $H_2O$ [zeolite P] $Na_2O \cdot Al_2O_3 \cdot 2$ $SiO_2 \cdot (3.5-10)H_2O$ (zeolite MAP) or the zeolites which can be represented by the partial or complete exchange of the Na atoms by Li atoms, K atoms or H atoms, typically $(Li,Na,K,H)_{10}Al_{10}Si_{22}O_{64} \cdot 20 H_2O$, $K_9Na_3[(AlO_2)_{12}(SiO_2)_{12}]$. $27 H_2O$, $K_4Al_4Si_4O_{16} \cdot 6H_2O$ [zeolite K—F], $Na_8Al_8Si_{40}O_{96} \cdot 24 H_2O$ zeolite such as described in Barrer et al., J. Chem. Soc. 1952, 1561–71, and in U.S. Pat. No. 2,950,952.

The following zeolites are also suitable: K offretite, such as described in EP-A-400 961; zeolite R, such as described in GB-A-841 812; zeolite LZ-217, as described in U.S. Pat. No. 4,503,023; calcium-free zeolite LZ-218, as described in U.S. Pat. No. 4,333,859; zeolite T, zeolite LZ-220, as described in U.S. Pat. No. 4,503,023; $Na_3K_6Al_9Si_{27}O_{72} \cdot 21 H_2O$ [zeolite L]; zeolite LZ-211, as described in U.S. Pat. No. 4,503,023; zeolite LZ-212, as described in U.S. Pat. No. 4,503,023; zeolite O, zeolite LZ-217, as described in U.S. Pat. No. 4,503,023; zeolite LZ-219, as described in U.S. Pat. No. 4,503,023; zeolite Rho, zeolite LZ-14, as described in U.S. Pat. No. 4,503,023; zeolite ZK-19, as described in Am. Mineral. 54 1607 (1969); zeolite W (K—M), as described in Barrer et al. J. Chem. Soc. 1956, 2882; $Na_{30}Al_{30}Si66O_{192} \cdot 98 H2O$ [zeolite ZK-5, zeolite Q]; as well as $AlPO_4$ compounds with zeolite structure.

It is preferred to use zeolite P types of formula

wherein x is 2 to 5, and y is 3.5 to 10, and M is an alkali metal atom and, very particularly preferably, zeolite MAP of formula IVa, wherein x is 2 and y is 3.5 to 10. Preferred is zeolite Na—P, i.e. M is Na. This zeolite is usually obtained in the variants Na—P-1, NaP-2 and Na—P-3, which differ from each other in their cubical, tetragonal or orthorhombic structure (R. M. Barrer, B. M. Munday, J.Chem.Soc. A 1971, 2909–14). The above-mentioned literature also describes the preparation of zeolite P-1 and P-2. According to this literature, zeolite P-3 is very rare and is therefore hardly of any practical interest. The structure of zeolite P-1 corresponds to the gismondite structure known from the above Atlas of Zeolite Structures. The more recent literature (EP-A-384 070) makes a difference between the cubical (zeolite B or $P_c$) and the tetragonal (zeolite $P_1$) zeolite of the P type. It also mentions newer zeolites of the P type having Si:Al ratio of less than 1.07:1. These zeolites are called MAP or MA-P for "maximum aluminium P". Depending on the method of preparation, zeolite P can contain minor amounts of other zeolites. A very pure zeolite P is described in WO-A-94/26662.

Within the scope of this invention, it is also possible to use those finely particulate water-insoluble sodium alumosilicates which were precipitated and crystallised in the presence of water-soluble inorganic or organic dispersants. These may be added to the reaction mixture in any manner before or during precipitation or crystallisation Sodium zeolite A, sodium zeolite P, sodium zeolite X and sodium zeolite Y are particularly preferred.

The hydrotalcites and zeolites can also be naturally occurring minerals or synthetically obtained compounds.

The hydrotalcites and/or zeolites can be used in amounts of e.g. 0.1 to 50, conveniently of 0.1 to 10 and, preferably, of 0.1 to 5, parts by weight, based on 100 parts by weight of halogen-containing polymer.

j) Alkalialumocarbonates (Dawsonites)

These compounds may be represented by formula $$\{(M_2O)_m.(Al_2O_3)_n.Z_o.pH_2O\} \tag{V},$$

wherein M is H, Li, Na, K, $Mg_{1/2}$, $Ca_{1/2}$, $Sr_{1/2}$ or $Zn_{1/2}$; Z is $CO_2$, $SO_2$, $(Cl_2O_7)_{1/2}$, $B_4O_6$, $S_2O_2$ (thiosulfate) or $C_2O_2$ (oxalate); m, if M=$Mg_{1/2}$ or $Ca_{1/2}$, is a number from 1 to 2, and in all other cases a number from 1 to 3; n is a number from 1 and 4; o is a number from 2 to 4; and p is a number from 0 to 30.

The alumo salt compounds of formula (V) which may be used can be naturally occurring minerals or synthetically prepared compounds. The metals can be partially exchanged for each other. The cited alumo salt compounds are crystalline, partially crystalline or amorphous or can be in the form of a dried gel. The alumo salt compounds can also be obtained in rarer crystalline modifications. EP 394670 describes a method for the preparation of such compounds. Typical examples of naturally occurring alumo salt compounds are indigirite, tunisite, alumohydrocalcite, para-alumohydrocalcite, strontiodresserite and hydrostrontio-dresserite. Other examples of alumo salt compounds are potassium alumocarbonate $\{(K_2O).(Al_2O_3).(CO_2)_2.2H_2O\}$, sodium alumothiosulfate $\{(Na_2O).(Al_2O_3).(S_2O_2)_2.2H_2O\}$, potassium alumosulfite $\{(K_2O).(Al_2O_3).(SO_2)_2.2H_2O\}$, calcium alumooxalate $\{(CaO).(Al_2O_3).(C_2O_2)_2.5H_2O\}$, magnesium alumotetraborate $\{(MgO).(Al_2O_3).(B_4O_6)_2.5H_2O\}$, $\{([Mg_{0.2}Na_{0.6}]_2O).(Al_2O_3).(CO_2)_2.4.1H_2O\}$, $\{([Mg_{0.2}Na_{0.6}]_2O).(Al_2O_3).(CO_2)_2.4.3H_2O\}$ and $\{([Mg_{0.3}Na_{0.4}]_2O).(Al_2O_3).(CO_2)_{2.2}.4.9H_2O\}$.

The mixed alumosalt compounds can be obtained by methods known per se by cation exchange, preferably from the alkali metal alumo salt compounds or by combination precipitation (see, for example, U.S. Pat. No. 5,055,284).

Preferred alumo salt compounds are those of the above formula, wherein M is Na or K; Z is $CO_2$, $SO_2$ or $(Cl_2O_7)_{1/2}$; m is 1–3; n 1–4; o is 2–4, and p is 0–20. Z is particularly preferably $CO_2$.

Other preferred compounds are those which can be represented by the following formulae:

$$M_2O.Al_2O_3.(CO_2)_2.pH_2O \tag{Ia},$$

$$(M_2O)_2.(Al_2O_3)_2.(CO_2)_2.pH_2O \tag{Ib},$$

$$M_2O.(Al_2O_3)_2.(CO_2)_2.pH_2O \tag{Ic},$$

where M is a metal, such as Na, K, $Mg_{1/2}$, $Ca_{1/2}$, $Sr_{1/2}$ or $Zn_{1/2}$, and p is a number from 0 to 12.

Sodium alumodihydroxycarbonate (DASC) and the homologous potassium compound (DAPC) are particularly preferred.

Instead of the dawsonites, it is also possible to use silicates having cation exchanger properties, such as bentonites, magadiite, haremite, and the like.

The dawsonites can be used in an amount of e.g. 0.01 to 50, conveniently of 0.1 to 10, particularly preferably of 0.1 to 5, parts by weight, based on 100 parts by weight of halogen-containing polymer.

k) Antioxidants

Suitable antioxidants are for example:

1. Alkylated monophenols, for example 2,6-di-tert-butyl-4-methylphenol, 2-tert-butyl-4,6-di-methylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-di-methylphenol, 2,6-dioctadecyl-4-methylphenol, 2,4,6-tricyclohexylphenol, 2,6-di-tert-butyl-4-methoxymethylphenol, 2,6-di-nonyl-4-methylphenol, 2,4-dimethyl-6-(1'-methylundec-1'-yl)phenol, 2,4-dimethyl-6-(1'-methylheptadec-1'-yl)phenol, 2,4-dimethyl-6-(1'-methyltridec-1'-yl)phenol and mixtures thereof.

2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis(3,5-di-tert-butyl-4-hydroxyphenyl) adipate.

4. Tocopherols, for example α-tocopherol, β-tocopherol, γ-tocopherol, δ-tocopherol and mixtures thereof (Vitamin E).

5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis(3,6-di-sec-amylphenol), 4,4'-bis(2,6-dimethyl-4-hydroxyphenyl) disulfide.

6. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis-(5-tert-butyl-4-hydroxy-2-methyl-phenyl)-3-n-dodecylmercaptobutane, ethylene glycol bis[3,3-bis(3'-tert-butyl-4'-hydroxyphenyl)butyrate], bis(3-tert-butyl-4-hydroxy-5-methylphenyl)dicyclopentadiene, bis[2-(3'-tert-butyl-2'-hydroxy-5'-methylbenzyl)-6-tert-butyl-4-methylphenyl]terephthalate, 1,1-bis(3,5-dimethyl-2-hydroxyphenyl)butane, 2,2-bis(3,5-di-tert-butyl-4-hydroxyphenyl)propane, 2,2-bis(5-tert-butyl-4-hydroxy-2-methylphenyl)-4-n-dodecylmercaptobutane, 1,1,5,5-tetra-(5-tert-butyl-4-hydroxy-2-methylphenyl)pentane.

7. O-, N- and S-benzyl compounds, for example 3,5,3',5'-tetra-tert-butyl-4,4'-dihydroxydibenzyl ether, octadecyl-4-hydroxy-3,5-dimethylbenzylmercaptoacetate, tris(3,5-di-tert-butyl-4-hydroxybenzyl)amine, bis(4-tert-butyl-3-hydroxy-2,6-dimethylbenzyl)dithioterephthalate, bis(3,5- di-tert-butyl-4-hydroxybenzyl)sulfide, isooctyl-3,5-di-tert-butyl-4 hydroxybenzylmercaptoacetate.
8. Hydroxybenzylated malonates, for example dioctadecyl-2,2-bis(3,5-di-tert-butyl-2-hydroxybenzyl)malonate, di-octadecyl-2-(3-tert-butyl-4-hydroxy-5-methylbenzyl) malonate, di-dodecylmercaptoethyl-2,2-bis(3,5-di-tert-butyl-4-hydroxybenzyl)malonate, bis[4-(1,1,3,3-tetramethylbutyl)phenyl]-2,2-bis(3,5-di-tert-butyl-4-hydroxybenzyl)malonate.
9. Aromatic hydroxybenzyl compounds, for example 1,3,5-tris(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.
10. Triazine Compounds, for example 2,4-bis (octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis (3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris-(3,5-di-tert-butyl-4-hydroxybenzyl) isocyanurate, 1,3,5-tris(4-tert-butyl-3-hydroxy-2,6-dimethylbenzyl)isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl) isocyanurate.
11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl-3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid.
12. Acylaminophenols, for example 4-hydroxylauranilide, 4-hydroxystearanilide, octyl N-(3,5-di-tert-butyl-4-hydroxyphenyl)carbamate.
13. Esters of β-(3,5-di-tert-butyl-4-hydroxyphenyl) propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris (hydroxyethyl) isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2] octane.
14. Esters of β-(5-tert-butyl-4-hydroxy-3-methylphenyl) propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris (hydroxyethyl) isocyanurate, N,N'-bis-(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2] octane.
15. Esters of β-(3,5-dicyclohexyl-4-hydroxyphenyl) propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris (hydroxyethyl) isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2] octane.
16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2] octane.
17. Amides of β-(3,5-di-tert-butyl-4-hydroxyphenyl) propionic acid e.g. N,N'-bis(3,5-di-tertbutyl-4-hydroxyphenylpropionyl)hexamethylenediamine, N,N'-bis(3,5-di-tert-butyl-4-hydroxyphenylpropionyl) trimethylenediamine, N,N'-bis(3,5-di-tert-butyl-4-hydroxyphenylpropionyl)hydrazine.

If desired, it is also possible to use a mixture of antioxidants of different structure. The antioxidants can be used in an amount of e.g. 0.01 to 10, conveniently of 0.05 to 5 and, preferably, of 0.05 to 3, parts by weight, based on 100 parts by weight of halogen-containing polymer.

I) UV Absorbers and other Light Stabilisers
Typical examples thereof are:

1. 2-(2'-Hydroxyphenyl)benzotriazoles, for example 2-(2'-hydroxy-5'-methylphenyl)benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chlorobenzotriazole, 2-(3'-tert-butyl-2'-hydroxy-5'-methylphenyl)-5-chlorobenzotriazole, 2-(3'-sec-butyl-5'-tert-butyl-2'-hydroxyphenyl)benzotriazole, 2-(2'-hydroxy-4'-octyloxyphenyl)benzotriazole, 2-(3',5'-di-tert-amyl-2'-hydroxyphenyl)benzotriazole, 2-(3',5'-bis(α,α-dimethylbenzyl)-2'-hydroxyphenyl)benzotriazole, mixture of 2-(3'-tert-butyl-2'-hydroxy-5'-(2-octyloxycarbonylethyl)phenyl)-5-chlorobenzotriazole, 2-(3'-tert-butyl-5'-[2-(2-ethylhexyloxy)-carbonylethyl]-2'-hydroxyphenyl)-5-chlorobenzotriazole, 2-(3'-tert-butyl-2'-hydroxy-5'-(2-methoxycarbonylethyl)phenyl)-5-chlorobenzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl) benzotriazole, 2-(3'-tert-butyl-5'-[2-(2-ethyl-hexyloxy) carbonylethyl]-2'-hydroxyphenyl)benzotriazole, 2-(3'-dodecyl-2'-hydroxy-5'-methylphenyl)benzotriazole, and 2-(3'-tert-butyl-2'-hydroxy-5'-(2-isooctyloxycarbonylethyl)phenylbenzotriazole, 2,2'-methylene-bis[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300;

where R=3'-tert-butyl-4'-hydroxy-5'-2H-benzotriazol-2-ylphenyl.

2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

3. Esters of substituted and unsubstituted benzoic acids, as for example 4-tert-butyl-phenyl salicylate, phenyl salicylate, octylphenyl salicylate, dibenzoyl resorcinol, bis(4-tert-butylbenzoyl)resorcinol, benzoyl resorcinol, 2,4-di-tertbutylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxy-cinnamate, butyl α-cyano-β-methyl-p-methoxy-cinnamate, methyl α-carbomethoxy-p-methoxycinnamate and N-(β-carbomethoxy-β-cyanovinyl)-2-methylindoline.

5. Nickel compounds, for example nickel complexes of 2,2'-thiobis[4-(1,1,3,3-tetra-methylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenyl undecylketoxime, nickel complexes of 1-phenyl-4-lauroyl-5-hydroxypyrazole, with or without additional ligands.

6. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxyanilide and its mixture with 2-ethoxy-2'-ethyl-5,4'-di-tert-butoxanilide and mixtures of ortho- and paramethoxy-disubstituted oxanilides and mixtures of o- and p-ethoxy-disubstituted oxanilides.

7. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis (2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)- 1,3,5-triazine, 2-(2-hydroxy-4-dodecyloxyphenyl)-4,6-bis(2,4-dimethylphenyl)-1,3,5-triazine, 2-[2-hydroxy-4-(2-hydroxy-3-butyloxy-propoxy)phenyl]-4,6-bis(2,4-dimethyl)-1,3,5-triazine, 2-[2-hydroxy-4-(2-hydroxy-3-octyloxy-propyloxy)phenyl]-4,6-bis(2,4-dimethyl)-1,3,5-triazine.

8. Sterically hindered amines, which are generally compounds of the alkyl or polyalkylpiperidine series containing at least one 2,2,6,6-tetramethyl- or 1,2,2,6,6-pentamethylpiperidinyl group, or/and a AYN group, wherein A and Y are each independently of the other $C_1$–$C_8$-alkyl, $C_3$–$C_8$alkenyl, $C_5$–$C_8$cycloalkyl or $C_7$–$C_9$phenylalkyl or together are $C_2$–$C_5$alkylene which is interrupted by O, NH or $CH_3$—N. Sterically hindered amines are, for example, N,N'-diacetyl-N,N'-bis[2,2,6,6-tetramethylpiperidin-4-yl]ethylenediamine; N,N'-bis[2,2,6,6-tetra-methylpiperidin-4-yl]oxamide; N,N'-bis[2,2,6,6-tetramethylpiperidin-4-yl]phthalic acid diamide; N,N'-bis[2,2,6,6-tetramethylpiperidin-4-yl]benzene-1,3-dicarboxylic acid diamide; N,N'-bis[2,2,6,6-tetramethylpiperidin-4-yl]adipinic acid diamide; N,N'-diacetyl-N,N'-bis[2,2,6,6-tetramethylpiperidin-4-yl] propylene-1,3-diamine; N,N'-diformyl-N,N'-bis[2,2,6,6-tetramethylpiperidin-4-yl]hexylene-1,6-diamine; N,N'-diacetyl-N,N'-bis-[2,2,6,6-tetramethylpiperidin-4-yl] hexylene-1,6-diamine; adipic acid-bis[4-hydroxy-2,2,6,6-tetramethylpiperidinyl] ester; poly(4'-tert-octylamino-2', 6'-N,N'-bis[2,2,6,6-tetramethylpiperidin-4-yl] hexamethylene-1,6-diamino-[1,3,5]triazine); poly(4'-morpholino-2',6'-N,N'-bis-[2,2,6,6-tetramethylpiperidin-4-yl]hexamethylene-1,6-diamino-[1,3,5]triazine); poly (4'-cyclohexylamino-2'-N,N'-bis[2,2,6,6-tetramethylpiperidin-4-yl]hexamethylene-1,6-diamino-[1,3,5]-triazine); poly(4'-piperidinyl-2',6'-N,N'-bis[2,2,6, 6-tetramethylpiperidin-4-yl]hexamethylene-1,6-diamino-[1,3,5]triazine); tris(2-hydroxy-3-N-[2,2,6,6-tetramethylpiperidin-4-yl]aminopropyl)isocyanurate; N,N',N",N'"-tetrakis(2',4'-bis[1,2,2,6,6-pentamethylpiperidin-4-yl-butylamino]-1,3,5-triazinyl)-1",2"-bis]3"'-methylaminopropylamino]ethane; tris[2'-di-i-propylaminoethylamino]-[1,3,5]triazine; N,N'-bis[2'-di-i-propylaminoethyl]adipic acid diamide; tris[2,2,6,6-tetramethylpiperidin-4-yl-amino]-[1,3,5]triazin; tris[3'-diethylaminopropylamino]-[1,3,5]triazine; 2'-[2,2,6,6-tetramethylpiperidin-4-yl-amino]-4',6'-diamino-[1,3,5] triazine; 2',4'-bis[2,2,6,6-tetramethylpiperidin-4-yl-amino]-6'-diethylamino-[1,3,5]triazine; 2',4'-bis[2,2,6,6-tetramethylpiperidin-4-yl-amino]-6'-morpholino-[1,3,5] triazine; poly(N,N',N",N'"-tetrakis-[2,2,6,6-tetramethylpiperidin-4-yl] acetylhexamethylenediaminoacetylhexamethylenediamine).

The concentration of UV absorbers and light stabilisers in the novel compositions is preferably in the same range as that indicated above for the antioxidants.

m) Plasticisers

Suitable organic plasticiser are, for example, those of the following groups:

A) Phthalates:

Typical examples of such plasticisers are dimethyl phthalate, diethyl phthalate, dibutyl phthalate, dihexyl phthalate, di-2-ethylhexyl phthalate, di-n-octyl phthalate, di-iso-octyl phthalate, di-iso-nonyl phthalate, di-iso-decyl phthalate, di-iso-tridecyl phthalate, dicyclohexyl phthalate, di-methylcyclohexyl phthalate, dimethyl glycol phthalate, dibutyl glycol phthalate, benzylbutyl phthalate and diphenyl phthalate as well as mixtures of phthalates, such as $C_{7-9}$- and $C_{9-11}$alkylphthalates of predominantly linear alcohols, $C_{6-10}$-n-alkylphthalates and $C_{8-10}$-n-alkylphthalates. Of these are preferred dibutyl phthalate, dihexyl phthalate, di-2-ethylhexyl phthalate, di-n-octyl phthalate, di-iso-octyl phthalate, di-iso-nonyl phthalate, di-iso-decyl phthalate, di-iso-tridecyl phthalate and benzylbutyl phthalate as well as the cited mixtures of alkyl phthalates. Particularly preferred are di-2-ethylhexyl phthalate, di-iso-nonyl phthalate and di-iso-decyl phthalate, which are also known by their standard abbreviations DOP (dioctyl phthalate, di-2-ethylhexyl phthalate), DINP (diisononyl phthalate), DIDP (di-isodecyl phthalate).

B) Esters of aliphatic dicarboxylic acids, in particular esters of adipic acid, azelaic acid and sebaccic acid Typical examples of such plasticisers are di-2-ethylhexyladipate, di-isooctyladipate (mixture), di-isononyl adipate (mixture), di-isodecyl adipate (mixture), benzyl butyl adipate, benzyl octyl adipate, di-2-ethylhexyl azelate, di-2-ethylhexyl sebacate and di-isodecyl sebacate (mixture). Di-2-ethylhexyl adipate and di-isooctyl adipate are preferred.

C) Trimellitates

Typically tri-2-ethylhexyl trimellitate, tri-isodecyltrimellitate (mixture), tri-isotridecyl trimellitate, triisooctyltrimellitate (mixture) as well as tri-$C_{6-8}$alkyl trimellitate, tri-$C_{6-10}$alkyl trimellitate, tri-$C_{7-9}$alkyl trimellitate and tri-$C_{9-11}$alkyl trimellitate. The last-mentioned trimellitates are obtained by esterifying the trimellitic acid with the corresponding alkanol mixtures. Preferred trimellitates are tri-2-ethylhexyl trimellitate and the cited trimellitates of alkanol mixtures. Standard abbreviations used are TOTM (trioctyl trimellitate, tri-2-ethylhexyl trimellitate), TIDTM (triisodecyl trimellitate) and TITDTM (triisotridecyl trimellitate).

D) Epoxide Plasticisers

These are mainly the epoxidised unsaturated fatty acid, such as epoxidised soy bean oil.

E) Polymeric Plasticisers

The most customary starting materials used for the preparation of the polyester plasticisers are: dicarboxylic acid, such as adipic acid, phthalic acid, azelaic acid and sebaccic acid; diols, such as 1,2-propanediol, 1,3-butanediol, 1,4-butanediol, 1,6-hexanediol, neopentyl glycol and diethylene glycol.

F) Phosphoric Acid Esters

Typical examples of such phosphoric acid esters are tributyl phosphate, tri-2-ethylbutyl phosphate, tri-2-ethylhexyl phosphate, trichlorethyl phosphate, 2-ethylhexyldi-phenyl phosphate, cresyldiphenyl phosphate, triphenyl phosphate, tricresyl phosphate and trixyleneyl phosphate. Tri-2-ethylhexyl phosphate and ®Reofos 50 and 95 (ex. FMC) are preferred.

G) Chlorinated Hydrocarbons (Paraffins)

H) Hydrocarbons

J) Monoesters, e.g. Butyl Oleate, Phenoxyethyl Oleate, Tetrahydrofurfuryl Oleate and Alkyl Sulfonate.

J) Glycol Esters, e.g. Diglycol Benzoate.

Definitions and examples of plasticisers of groups A) to J) are to be found in the following reference books:

"Taschenbuch der Kunststoffadditive", edited by R. Gächter and H. Müller, Carl Hanser Verlag, 1989, chapter 5 S 341–442.

"PVC Technology", editor W. V. Titow, 4th Ed., Elsevier Publishers, 1984, chapter 6, pages 147–180.

It is also possible to use mixtures of different plasticisers. The plasticisers can be used in an amount of e.g. 5 to 120, conveniently of 10 to 100, parts by weight, based on 100 parts by weight of PVC.

n) Suitable Lubricants are for Example:

Montan wax, fatty acid ester, PE waxes, amide waxes, chloroparaffin, glycerol ester, solid or liquid paraffin waxes or alkaline earth metal soaps, or lubricants based on silicone, such as described in EP-A-225261. Lubricants which can be used are also described in "Taschenbuch der Kunststoffadditive", edited by R. Gächter and H. Müller, Carl Hanser Verlag, 3rd Ed. 1989, pages 478–488. Prior to being added to the polymeric materials, the lubricants can also be blended with the stabilisers.

o) Fillers

Suitable fillers ("Handbook of PVC-Formulating", by E. J. Wickson, John Wiley & Sons, New York 1993, p.393–449) and reinforcing agents ("Taschenbuch der Kunststoffadditive", editors R. Gächter and H. Müller, Carl Hanser Verlag, 3rd Ed. 1989, pages 549–615) can be for example: calcium carbonate, dolomite, wollastonite, magnesium oxide, magnesium hydroxide, silicates, glass fibres, talcum, kaolin, chalk, mica, metal oxides and metal hydroxides, carbon black or graphite. Chalk is preferred.

p) Pigments

Suitable materials are known to the skilled person. Typical examples of inorganic pigments are $TiO_2$, carbon black, $Fe_2O_3$, $Sb_2O_3$, $(Ti,Ba,Sb)O_2$, $Cr_2O_3$, spinells, such a cobalt blue and cobalt green, $Cd(S,Se)$, ultramarine blue. $TiO_2$, also in micronised form, is preferred. Organic pigments are, for example, azo pigments, phthalocyanine pigments, quinacridone pigments, perylene pigments, pyrrolopyrrylidone pigments and anthraquinone pigments. Further details are to be found in "Handbook of PVC Formulating", E. J. Wickson, John Wiley & Sons, New York 1993, p. 449–474.

q) Organotin Compounds

The organotin compounds are, for example, organotin oxides, organotin sulfides, organotin carboxylates, organotin mercaptocarboxylates, organotin mercaptides and/or organotin mercaptocarboxylates, such as dibutyltin oxide, dioctyltin maleinate, dibutyltin maleic acid semiester, bis-dibutyltin-2-ethylhexanoate oxide and other SnO compounds, such as desribed, inter alia, in EP-A-573394.

Suitable organotin mercaptides are, for example, compounds of the general structure $R_nSn(SA)_{n-4}$, wherein R is, inter alia, a methyl, butyl, octyl, lauryl or carbobutoxyethyl group, n is 1 or 2, nd A is typically a decyl, dodecyl or carboalkoxymethyl or carboalkyloxyethyl radical, and the alkoxy moiety is a straight-chain or branched $C_6$–$C_{18}$alkoxy or $C_5$–$C_8$cycloalkoxy radical. Illustrative examples of such tin compounds are dimethyltin bis-carboisooctyloxymethyl mercaptide, dibutyltin dilauryl mercaptide, dioctyltin bis-carbo-2-ethylhexoxymethyl mercaptide, dimethyltin bis-mercaptoethyl stearate, octyltin tris-carbo-2-ethylhexoxymethyl mercaptide, monomethyltin mercaptoethyl oleate sulfide and bis-dimethyltin mercaptoethyl stearate sulfide.

r) Organic Nitrogen Compounds

Suitable organic nitrogen compounds are, for example, ureas and thioureas, aminobenzene sulfonates, aminobenzoates, aminobenzamides, cyanamides, dicyandiamides, guanidines, guanamines, melamines, indoles, aminocrotonates, tetrazoles, triazoles, substituted aminotriazoles, m-aminophenols, aminouracils, pyrroles, aminopyrroles, and others, such as described, inter alia, in DE-A-746 081, U.S. Pat. No. 2,557,474, DD-A-652, DE-A-871 834, EP-A-1 74 412, DE-A-1 162 073, U.S. Pat. No. 2,367,483, GB-A-923 319, DE-A-862 512, DE-A-2 524 659, DE-A-1 544 768, DE-A-1 134 197, EP-A-2 756, DE-A-3 048 659, DE-A-3 602 367, EP-A-48 222, EP-A-41 479, EP-A-65 934, EP-A-22 087, EP-A-465 405 and EP-A-390 739.

Preferred novel compositions comprise as additional component(s) (iii) a zinc compound of formula $ZnR_5R_6$, wherein $R_5$ and $R_6$ are identical or different and are $C_1$–$C_{22}$alkyl-COO, phenyl-COO, $C_1$–$C_{12}$alkyl-substituted phenyl-COO, $C_5$–$C_8$cycloalkyl-COO, OH, Cl, $C_1$–$C_{22}$alkyl-O—C(O)—[$CH_2$]$_p$—S— or

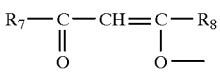

or, taken together, are O, S or $CO_3$, and $R_7$ and $R_8$ are a hydrocarbon radical, and p is a number from 1 to 3; or/and a sterically hindered amine containing one or more than one 2,2,6,6-tetramethylpiperidine group; or/and an organotin compound from the series of the organotin sulfides, organotin mercaptides or organotin mercaptocarboxylates; or/and an organic nitrogen compound from the series of the 3-aminocrotonates, 2-phenylindoles, pyrroles or aminouracils.

In another of its aspects, this invention relates to the use of phosphites of formula I for stabilising halogen-containing polymeric material, in particular polyvinyl chloride, as well as to a process for stabilising halogen-containing polymeric material, which comprises incorporating into this material at least one compound of formula I.

The compounds of formula I and further optional additives can be added to the polymers in known manner, mixing said compounds and further optional additives with the halogen-containing polymer using known apparatus such as mixers, calenders, kneaders, extruders, mills and the like. In this process they can be added singly or in admixture, or also in the form of so-called masterbatches. The novel polymer compositions can be brought into the desired shape by known methods, such as calendering, extruding, injection moulding, sintering or spinning, and also by extrusion blow moulding or processing by the plastisol process. The polymer compositions can also be processed to foams.

The novel compositions are suitable e.g. for semirigid or soft formulations, for example for soft formulations for wire sheaths, cable insulations, floorings, tubes and sealing profiles. In the form of semirigid formulations, said novel polymer compositions are suitable for decorative films, foams, agricultural sheeting, tubes, sealing profiles, office films, extruded profiles and plates, flooring films and panels, coating materials and artificial leather as well as crash-pad films (for use in automobiles). In the form of rigid formulations, the novel compositions are suitable for hollow articles (bottles), packaging films, thermoforming films, blown films, crash-pad films (automobiles), pipes, foams, heavy profiles (window frames), light-wall profiles, building profiles, sidings, fittings, and apparatus housings (computers and domestic appliances) as well as other injection moulded articles. Examples of the use of the compositions stabilised according to this invention as plastisols are artificial leather, coating materials, floorings, textile coatings, wall coverings, coil coatings, crash-pad films and automotive underseals.

Examples of sintered applications of the polymer compositions stabilised according to this invention are slush, slush mould and coil coatings.

The compounds of formula I are either known, e.g. from some of the publications indicated at the outset, or can be prepared in general analogy to the processes described therein or in Houben-Weyl, "Methoden der Organischen Chemie", Vol. XII/2, pages 53–62 and 73–78, G. Thieme Verlag, Stuttgart, 1964. Their preparation is typically carried out by reacting phosphorus trichloride with a diol of formula HO—R—OH and an alcohol or alcohol mixture of formula $R_1OH$, $R_2OH$, $R_3OH$, or/and $R_4OH$, preferably in nonpolar solvents and in the presence of bases, preferably of tertiary amines, as HCl acceptors.

The preparation of compounds of formula I is particularly conveniently effected by reacting a triaryl phosphite, typically of triphenyl phosphite or trisnonylphenyl phosphite, with a diol of formula HO—R—OH and an alcohol or alcohol mixture of formula $R_1OH$, $R_2OH$, $R_3OH$ or/and $R_4OH$. It is advantageous to work in the presence of a transesterifcation catalyst, typically a base, such as an alkali metal hydroxide or alkali metal alcoholate, e.g. sodium methylate. In both processes, the molar ratio of phosphorus trichloride or triaryl phosphite:diol:alcohol is about 2:1:4, minor excesses of one or the other components being possible.

To prepare compounds of formula I, wherein $R_1$ and $R_2$ or/and $R_3$ and $R_4$, taken together, are each an alkylene radical, it may also be useful to react a cyclic compound of formula

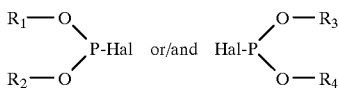

(Hal is a halogen atom, preferably chloro), typically an unsubstituted or alkyl-substituted chlorophosphorinane of formula

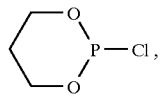

with a diol of formula HO—R—OH. In this reaction, it is advantageous to add a base as hydrogen halide scavenger, typically a tertiary amine. Processing is preferably carried out in the presence of a solvent, e.g. toluene, heptane or tetrahydrofuran.

To prepare compounds of formula I mit n>1, it is preferred to use the above transesterification process and the molar ratio of the triaryl phosphite, HO—R—OH and $R_1OH$, $R_2OH$, $R_3OH$, $R_4OH$ components is adjusted correspondingly.

This preparation often results naturally in mixtures of phosphites of formula I which can be separated, if desired, by customary physical separation methods, such as chromatography, recrystallisation and the like. However, such mixtures can also be incorporated direct into the novel compositions.

Further details concerning the preparation of compounds of formula I can be found in the Preparation Examples given later in the text.

This invention also relates to novel compounds of formula I, wherein R is a linking group of formula BR3, BR4 or BR6, and the other general symbols are as defined for formula I.

Those compounds of formula I are preferred, wherein $R_1$, $R_2$, $R_3$ and $R_4$ or $R_1+R_2$ and $R_3+R_4$ are each identical.

In these novel compounds, n is in particular 1 to 4, preferably 1to 3, most preferably 1.

Novel compounds of formula I to be mentioned in particular are those, wherein R is a linking group of formula BR3, BR4 or BR6, and $R_1$, $R_2$, $R_3$ and $R_4$ are $C_8$–$C_{18}$alkyl, or $R_1$ and $R_2$ and/or $R_3$ and $R_4$ together are $C_2$–$C_9$alkylene.

Another object of this invention are novel compounds of formula I, wherein n is a number from 2 to 6, R is a linking group BR1, BR2 or BR5, and the other general symbols are as defined for formula I, and wherein the provisos a) and b), indicated at the outset for formula I, do not apply. Particular mention is to be made of those novel compounds of this kind, wherein n is 2 to 5, as well as of those, wherein $R_1$, $R_2$, $R_3$ and $R_4$ are $C_8$–$C_{18}$alkyl, or $R_1$ and $R_2$ and/or $R_3$ and $R_4$ together are $C_2$–$C_9$alkylene.

The novel compounds of formula I described above are excellently suited for stabilising organic materials against oxidative, thermal or light-induced degradation.

Typical examples of such materials are:

1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), (VLDPE) and (ULDPE).

Polyolefins, i.e. the polymers of monoolefins exemplified in the preceding paragraph, preferably polyethylene and polypropylene, can be prepared by different, and especially by the following, methods:
  a) radical polymerization (normally under high pressure and at elevated temperature).
  b) catalytic polymerisation using a catalyst that normally contains one or more than one metal of groups IVb, Vb, VIb or VII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

5. Polystyrene, poly(p-methylstyrene), poly(α-methylstyrene).

6. Copolymers of styrene or α-methylstyrene with dienes or acrylic derivatives, for example styrene/butadiene, styrene/acrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

7. Graft copolymers of styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated and brominated copolymer of isobutylene-isoprene (halobutyl rubber), chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from α,β-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylontrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide, 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).
17. Polyureas; polyimides, polyamide-imides, polyetherimids, polyesterimids, polyhydantoins and polybenzimidazoles.
18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.
19. Polycarbonates and polyester carbonates.
20. Polysulfones, polyether sulfones and polyether ketones.
21. Crosslinked polymers derived from aldehydes on the one hand and phenols, ureas and melamines on the other hand, such as phenol/formaldehyde resins, urea/formaldehyde resins and melamine/formaldehyde resins.
22. Drying and non-drying alkyd resins.
23. Unsaturated polyester resins derived from copolyesters of saturated and unsaturated dicarboxylic acids with polyhydric alcohols and vinyl compounds as crosslinking agents, and also halogen-containing modifications thereof of low flammability.
24. Crosslinkable acrylic resins derived from substituted acrylates, for example epoxy acrylates, urethane acrylates or polyester acrylates.
25. Alkyd resins, polyester resins and acrylate resins crosslinked with melamine resins, urea resins, isocyanates, isocyanurates, polyisocyanates or epoxy resins.
26. Crosslinked epoxy resins derived from aliphatic, cycloaliphatic, heterocyclic or aromatic glycidyl compounds, e.g. products of diglycidyl ethers of bisphenol A and bisphenol F, which are crosslinked with customary hardeners such as anhydrides or amines, with or without accelerators.
27. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.
28. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO, PBT/PC/ABS or PBT/PET/PC.
29. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, typically those used as spinning compositions, as well as aqueous emulsions of such materials.
30. Aqueous emulsions of natural or synthetic rubber, e.g. natural latex or latices of carboxylated styrene/butadiene copolymers.
31. Petroleum distillation and carbon distillation residues, such as asphalt, bitumen or bituminous compounds for road surfaces.

The organic material to be protected is preferably natural, semi-synthetic or synthetic polymers, in particular synthetic polymers. Thermoplastic polymers are particularly preferred, especially polyvinyl chloride or polyolefins, typically polyethylene and polypropylene (PP).

Accordingly, this invention also relates to compositions comprising a synthetic or semi-synthetic organic polymer and at least one novel phosphite of formula I as defined above, to the use of said composition for stabilising the cited polymers, as well as to a process for stabilising synthetic or semi-synthetic organic polymers, which comprises incorporating therein at least one novel phosphite of formula I. Illustrative examples of polymers to be stabilised are to be found in the above list (No. 1–28 and 30). Of these, polyolefins, polyurethanes, polycarbonates, polyamides and elastomers are preferred.

The novel compounds of formula I are present in the compositions of this invention conveniently in an amount of 0.01 to 10, typically of 0.05 to 5, preferably of 0.05 to 3 and, most preferably, of 0.05 to 2, % by weight. They may be one or more than one compound of formula I and the percentages by weight are based on the total amount of these compounds.

Their incorporation into the materials can typically by effected by blending or applying the compounds of formula I and further optional additives by the customary methods of the art. The incorporation can be carried out before or after moulding, or by applying the dissolved or dispersed compounds to the polymer, if required with subsequent evaporation of the solvent. Elastomers may also be stabilised as latices. Another possibility of incorporating the compounds of formula I into polymers consists in adding them before, during or immediately after the polymerisation of the corresponding monomers or before crosslinking. In this process, the compounds of formula I can be added as they are or also in encapsulated form (e.g. in waxes, oils or polymers). Where they are added before or during the polymerisation, the compounds of formula I can also regulate the chain length of the polymers (chain terminators).

The compounds of formula I or mixtures thereof can also be added to the plastic materials to be stabilised in the form of a masterbatch which comprises these compounds in a concentration of e.g. 2.5 to 25% by weight.

The incorporation of the compounds of formula I can conveniently be effected by the following methods:

- as emulsion or dispersion (e.g. to latices or emulsion polymers),
- as dry mixture during the blending of additional components or polymer mixtures,
- by direct addition to the processing apparatus (e.g. extruder, internal mixer and the like),
- as solution or melt.

Polymer compositions according to this invention can be used in different forms or can be processed to different products e.g. as films, fibres, filaments, moulded articles, profiles, or as binders for paint systems, adhesives or putties.

As mentioned above, the organic material to be protected are semi-synthetic or synthetic, preferably synthetic, polymers. Thermoplastic polymers, in particular polyolefins, are protected particularly advantageously. The excellent effectivity of the compounds of formula I as processing stabilisers (heat stabilisers) is to be particularly highlighted. To this purpose they are usefully added before or while the polymer is processed.

However, it is also possible to stabilise other polymers (e.g. elastomers) or lubricants or hydraulic fluids against degradation, e.g. light-induced or/and thermooxidative degradation. Elastomers are to be found in the above list of possible organic materials.

In another of its aspects, this invention relates to compositions comprising a lubricant, a hydraulic fluid or metal processing fluid and at least one phosphite of formula I, to the use of such phosphites as additives in lubricants and in the cited functional fluids, as well as to a process for enhancing the performance properties of lubricants, hydraulic fluids or metal processing fluids, which comprises adding thereto at least one phosphite of formula I.

Suitable lubricants, metal processing fluids and hydraulic fluids are based, for example, on mineral or synthetic oils or mixtures thereof. The skilled person is familiar with the lubricants, which are described, inter alia, in Dieter Klamann, "Schmierstoffe and verwandte Produkte" (Verlag Chemie, Weinheim, 1982), in Schewe-Kobek, "Das Schmiermittel-Taschenbuch" (Dr. Alfred Hüthig-Verlag, Heidelberg, 1974) and in "Ullmanns Enzyklopädie der technischen Chemie", Vol. 13, pages 85–94 (Verlag Chemie, Weinheim, 1977).

The novel compositions, in particular if they comprise organic, preferably synthetic, polymers, can contain further customary additives, e.g. stabilisers, besides the novel compounds. Illustrative examples of such additives are:

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example, 2,6-di-nonyl-4-methylphenol, 2,4-dimethyl-6-(1'-methylundec-1'-yl)phenol, 2,4-dimethyl-6-(1'-methylheptadec-1'-yl)phenol, 2,4-dimethyl-6-(1'-methyltridec-1'-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis-(3,5-di-tert-butyl-4-hydroxyphenyl) adipate.

1.4. Tocopherols, for example α-tocopherol, β-tocopherol, γ-tocopherol, δ-tocopherol and mixtures thereof (Vitamin E).

1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis-(3,6-di-sec-amylphenol), 4,4'-bis(2,6-dimethyl-4-hydroxyphenyl)disulfide.

1.6. Alkylidenebisophenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)-phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl)butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis-(3,5-di-tert-butyl-4-hydroxyphenyl)propane, 2,2-bis-(5-tert-butyl-4-hydroxy2-methylphenyl)-4-n-dodecylmercaptobutane, 1,1,5,5-tetra-(5-tert-butyl-4-hydroxy-2-methylphenyl) pentane.

1.7. O-, N- and S-benzyl compounds, for example 3,5,3',5'-tetra-tert-butyl-4,4'-dihydroxydibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5-di-tert-butyl-4-hydroxybenzylmercaptoacetate.

1.8. Hydroxybenzylated malonates, for example dioctadecyl-2,2-bis-(3,5-di-tert-butyl-2-hydroxybenzyl)-malonate, di-octadecyl-2-(3-tert-butyl-4-hydroxy-5-methylbenzyl)-malonate, didodecylmercaptoethyl-2,2-bis-(3,5-di-tert-butyl-4-hydroxybenzyl)malonate, bis[4-(1,1,3,3-tetramethylbutyl)phenyl]-2,2-bis(3,5-di-tert-butyl-4-hydroxybenzyl)malonate.

1.9. Aromatic hydroxybenzyl compounds, for example 1,3,5-tris-(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.10. Triazine compounds, for example 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris-(3,5-di-tert-butyl-4-hydroxybenzyl)

isocyanurate, 1,3,5-tris(4-tert-butyl-3-hydroxy-2,6-dimethylbenzyl)isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl) isocyanurate.

1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3,5-di-tert-butyl-4-hydroxyphenyl) propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris (hydroxyethyl) isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2] octane.

1.14. Esters of β-(5-tert-butyl-4-hydroxy-3-methylphenyl) propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris (hydroxyethyl) isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2] octane.

1.15. Esters of β-(3,5-dicyclohexyl-4-hydroxyphenyl) propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris (hydroxyethyl)isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2] octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2] octane.

1.17. Amides of β-(3,5-di-tert-butyl-4-hydroxyphenyl) propionic acid e.g. N,N'-bis(3,5-di-tert-butyl-4-hydroxyphenylpropionyl)hexamethylenediamide, N,N'-bis(3,5-di-tert-butyl-4-hydroxyphenylpropionyl) trimethylenediamide, N,N'-bis(3,5-di-tert-butyl-4-hydroxyphenylpropionyl)hydrazine.

1.18. Ascorbic acid (vitamin C)

1.19. Aminic antioxidants, for example N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenlenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino]ethane, 1,2-bis(phenylamino)propane, (o-tolyl)biguanide, bis[4-(1',3'-dimethylbutyl)phenyl]amine, tert-octylated N-phenyl-1-naphthylamine, a mixture of mono- and dialkylated tert-butyl/tert-octyldiphenylamines, a mixture of mono- and dialkylated nonyldiphenylamines, a mixture of mono- and dialkylated dodecyldiphenylamines, a mixture of mono- and dialkylated isopropyl/isohexyldiphenylamines, a mixture of mono- und dialkylated tert-butyldiphenylamines, 2,3-dihydro-3,3-dimethyl-4H-1,4-benzothiazine, phenothiazine, a mixture of mono- und dialkylated tert-butyl/tert-octylphenothiazines, a mixture of mono- und dialkylated tert-octyl-phenothiazines, N-allylphenothiazin, N,N,N',N'-tetraphenyl-1,4-diaminobut-2-ene, N,N-bis-(2,2,6,6-tetramethyl-piperid-4-yl-hexamethylenediamine, bis(2,2,6,6-tetramethylpiperid-4-yl)sebacate, 2,2,6,6-tetramethylpiperidin-4-one, 2,2,6,6-tetramethylpiperidin-4-ol.

2. UV Absorbers and light stabilisers 2.1. 2-(2'-Hydroxyphenyl)benzotriazoles, for example 2-(2'-hydroxy-5'-methylphenyl)-benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxyphenyl)benzotriazole, 2-(2'-hydroxy-4'-octyloxyphenyl)benzotriazole, 2-(3',5'-di-tert-amyl-2'-hydroxyphenyl)benzotriazole, 2-(3',5'-bis-(α,α-dimethylbenzyl)-2'-hydroxyphenyl)benzotriazole, 2-(3'-tert-butyl-2'-hydroxy-5'-(2-octyloxycarbonylethyl) phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl)phenyl)-5-chloro-benzotriazole, 2-(3'-tert-butyl-2'-hydroxy-5'-(2-methoxycarbonylethyl) phenyl)benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole, 2-(3'-tert-butyl-2'-hydroxy-5'-(2-isooctyloxycarbonylethyl) phenylbenzotriazole, 2,2'-methylene-bis-[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300; [R—CH$_2$CH$_2$—COO—CH$_2$CH$_2$—]$_2$ where R=3'-tert-butyl-4'-hydroxy-5'-2H-benzotriazol-2-ylphenyl.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, as for example 4-tertbutyl-phenyl salicylate, phenyl salicylate, octylphenyl salicylate, dibenzoyl resorcinol, bis(4-tert-butylbenzoyl) resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxy-cinnamate, butyl α-cyano-β-methyl-p-methoxy-cinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thio-bis-[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenyl undecylketoxime, nickel complexes of 1-phenyl-4-lauroyl-5-hydroxypyrazole, with or without additional ligands.

2.6. Sterically hindered amines, for example bis(2,2,6,6-tetramethyl-4-piperidyl)sebacate, bis(2,2,6,6-tetramethyl-4-piperidyl)succinate, bis(1,2,2,6,6-pentamethyl-4-piperidyl)sebacate, bis(1-octyloxy-2,2,6,6-tetramethyl-4-piperidyl)sebacate, bis(1,2,2,6,6-pentamethyl-4-piperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, linear or cyclic condensates of N,N'-bis(2,2,6,6-tetramethyl-4-piperidyl) hexamethylenediamine and 4-tert-octylamino-2,6-dichloro-1,3,5-triazine, tris(2,2,6,6-tetramethyl-4-piperidyl)nitrilotriacetate, tetrakis-(2,2,6,6-tetramethyl-4-piperidyl)-1,2,3,4-butane-tetracarboxylate, 1,1'-(1,2-ethanediyl)-bis-(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4.5]decan-2,4-dione, bis(1-octyloxy-2,2,6,6-tetramethylpiperidyl)sebacate, bis(1-octyloxy-2,2,6,6-tetramethylpiperidyl)succinate, linear or cyclic condensates of N,N'-bis-(2,2,6,6-tetramethyl-4-piperidyl) hexamethylenediamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidin-2,5-dione, 3-dodecyl-1-(1,2,2,6,6-pentamethyl-4-piperidyl)pyrrolidine-2,5-dione, a mixture of 4-hexadecyloxy- and 4-stearyloxy-2,2,6,6-tetramethylpiperidine, a condensation product of N,N'-bis (2,2,6,6-tetramethyl-4-piperidyl)hexamethylenediamine and 4-cyclohexylamino-2,6-dichloro-1,3,5-triazine, a condensation product of 1,2-bis(3-aminopropylamino) ethane and 2,4,6-trichloro-1,3,5-triazine as well as 4-butylamino-2,2,6,6-tetramethylpiperidine (CAS Reg. No. [136504-96-6]); N-(2,2,6,6-tetramethyl-4-piperidyl)-n-dodecylsuccinimide, N-(1,2,2,6,6-pentamethyl-4-piperidyl)-n-dodecylsuccinimid, 2-undecyl-7,7,9,9-tetramethyl-1-oxa-3,8-diaza-4-oxo-spiro[4,5]decane, a reaction product of 7,7,9,9-tetramethyl-2-cycloundecyl-1-oxa-3,8-diaza-4-oxospiro [4,5]decane and epichlorohydrin.

2.7. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxy-propoxy)phenyl]-4,6-bis(2,4-dimethyl)-1,3,5-triazine, 2-[2-hydroxy-4-(2-hydroxy-3-octyloxy-propyloxy)phenyl]-4,6-bis(2,4-dimethyl)-1,3,5-triazine, 2-[4-(dodecyloxy/tridecyloxy-2-hydroxypropoxy)-2-hydroxy-phenyl]-4,6-bis(2,4-dimethylphenyl)-1,3,5-triazine, 2-[2-hydroxy-4-(2-hydroxy-3-dodecyloxy-propoxy)phenyl]-4,6-bis(2,4-dimethylphenyl)-1,3,5-triazine, 2-(2-hydroxy-4-hexyloxy)phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxy-propoxy)phenyl]-1,3,5-triazine, 2-(2-hydroxyphenyl)-4-(4-methoxyphenyl)-6-phenyl-1,3,5-triazine, 2-{2-hydroxy-4-[3-(2-ethylhexyl-1-oxy)-2-hydroxypropyloxy]phenyl}-4,6-bis(2,4-dimethylphenyl)-1,3,5-triazine.

3. Metal deactivators, for example N,N'-diphenyloxamide, N-salicylal-N'-salicyloyl hydrazine, N,N'-bis(salicyloyl) hydrazine, N,N'-bis(3,5-di-tert-butyl-4-hydroxyphenylpropionyl) hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl)oxalyl dihydrazide, N,N'-bis(salicyloyl)thiopropionyl dihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, bis(2,6-di-tert-butyl-4-methylphenyl)-pentaerythritol diphosphite, diisodecyloxypentaerythritol diphosphite, bis(2,4-di-tert-butyl-6-methylphenyl)pentaerythritol diphosphite, bis(2,4,6-tris(tert-butylphenyl)pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-di-benz[d,g]-1,3,2-dioxaphosphocin, 6-fluoro-2,4,8,10-tetra-tert-butyl-12-methyl-dibenz[d,g]-1,3,2-dioxaphosphocin, bis(2,4-di-tert-butyl-6-methylphenyl) methyl phosphite, bis(2,4-di-tert-butyl-6-methylphenyl) ethyl phosphite.

5. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

6. Nitrones, for example, N-benzyl-alpha-phenyl-nitrone, N-ethyl-alpha-methyl-nitrone, N-octyl-alpha-heptyl-nitrone, N-lauryl-alpha-undecyl-nitrone, N-tetradecyl-alpha-tridcyl-nitrone, N-hexadecyl-alpha-pentadecyl-nitrone, N-octadecyl-alpha-heptadecyl-nitrone, N-hexadecyl-alpha-heptadecyl-nitrone, N-ocatadecyl-alpha-pentadecyl-nitrone, N-heptadecyl-alpha-heptadecyl-nitrone, N-octadecyl-alpha-hexadecyl-nitrone, nitrone derived from N,N-dialkylhydroxylamine derived from hydrogenated tallow amine.

7. Thiosynergists, for example, dilauryl thiodipropionate or distearyl thiodipropionate.

8. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

9. Polyamide stabilisers, for example, copper salts in combination with iodides and/or phosphorus compounds and salts of divalent manganese.

10. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example calcium stearate, zinc stearate, magnesium behenate, magnesium stearate, sodium ricinoleate and potassium palmitate, antimony pyrocatecholate or zinc pyrocatecholate.

11. Nucleating agents, for example, inorganic substances such as talcum, metal oxides such as titanium dioxide or magnesium oxide, phosphates, carbonates or sulfates of, preferably, alkaline earth metals; organic compounds such as mono- or polycarboxylic acids and the salts thereof, e.g. 4-tert-butylbenzoic acid, adipic acid, diphenylacetic acid, sodium succinate or sodium benzoate; polymeric compounds such as ionic copolymers (ionomers).

12. Fillers and reinforcing agents, for example, calcium carbonate, silicates, glass fibres, glass bulbs, asbestos, talc, kaolin, mica, barium sulfate, metal oxides and hydroxides, carbon black, graphite, wood flour and flours or fibers of other natural products, synthetic fibers.

13. Other additives, for example, plasticisers, lubricants, emulsifiers, pigments, rheology additives, catalysts, flow-control agents, optical brighteners, flameproofing agents, antistatic agents and blowing agents.

14. Benzofuranones and indolinones, for example those disclosed in U.S. 4,325,863; U.S. Pat. No. 4,338,244; U.S. Pat. No. 5,175,312; U.S. Pat. No. 5,216,052; U.S. Pat. No. 5,252,643; DE-A-4316611; DE-A-4316622; DE-A-4316876; EP-A-0589839 or EP-A-0591102 or 3-[4-(2-acetoxyethoxy)phenyl]-5,7-di-tert-butyl-benzofuran-2-one, 5,7-di-tert-butyl-3-[4-(2-stearoyloxyethoxy)-phenyl] benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butyl-benzofuran-2-one, 3-(3,5-dimethyl-4-pivaloyloxyphenyl)-5,7-di-tert-butyl-benzofuran-2-one.

The following Examples illustrate the invention in more detail. Here as well as in the claims and throughout the remaining description, parts and percentages are by weight, unless otherwise stated.

EXAMPLE 1

Tetra(tridecyl/pentadecyl)dianhydrosorbitol Diphosphite

A reaction apparatus, which is well rinsed with anhydrous nitrogen and equipped with stirrer, thermometer, distillation bridge and condenser flask, is charged with 310.3 g (1.0 mol) of triphenyl phosphite, 73.1 g (0.5 mol) of 1,4,3,6-dianhydrosorbitol, 422.0 g (2.0 mol) of a tridecyl-/pentadecyl alcohol mixture (®ACROPOL-35) and 2.7 g (0.05 mol) of sodium methylate, and this mixture is then heated over one hour to 110° C. and stirred for 3 hours at 110° C.

The mixture is cooled to 80° C. and then, while slowly increasing the temperature to 150° C., the greater part of the released phenol is distilled off under vacuum and the remaining phenol is drawn off over one hour using an oil pump at 150° C. and c. 0.1 mbar.

The residue is charged with 2 g of filter aid and is then filtered. 502.3 g of a pale yellow liquid are obtained, the structure and analytical values of which are indicated in the following Table under Example 1.

Repeating the above procedure, but using the corresponding diols and monoalcohols, or the mixtures thereof, gives the phosphites indicated in Table 1, Examples 2–7.

TABLE 1 phosphite: 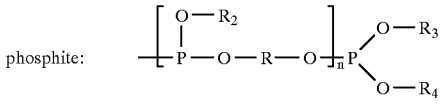

(n = 1)

| Example | R | $R_1, R_2, R_3, R_4$ | yield % of theory | $n_D^{20}$ | % P calcd./found |
|---|---|---|---|---|---|
| 1 | 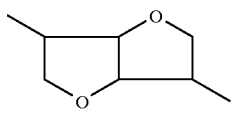 | $R_1 = R_2 = R_3 = R_4 =$<br>$C_{13}H_{27}/C_{15}H_{31}$— | 97 | 1.4700 | 6.01/5.88 |
| 2 | —$[CH-CH_2]_2O$<br>\|<br>$CH_3$ | $R_1 = R_2 = R_3 = R_4 =$<br>i-$C_{10}H_{21}$— | 88 | 1.4620 | 7.53/7.59 |
| 3 | —$[CH-CH_2]_2O$<br>\|<br>$CH_3$ | $R_1 = R_2 = R_3 = R_4 =$<br>$C_{12}H_{25}/C_{14}H_{29}$— | 90 | 1.4627 | 6.19/6.05 |
| 4 | —$[CH-CH_2]_2O$<br>\|<br>$CH_3$ | $R_1 = R_2 = R_3 = R_4 =$<br>i-$C_8H_{17}$— | 84 | 1.4645 | 8.71/8.76 |
| 5 | 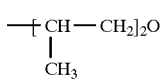 | $R_1 = R_2 = R_3 = R_4 =$<br>i-$C_{10}H_{21}$— | 83 | 1.4837 | 7.00/7.22 |
| 6 | 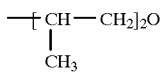 | $R_1 = R_2 = R_3 = R_4 =$<br>$C_4H_9$—CH—$CH_2$—<br>\|<br>$C_2H_5$ | 84 | 1.4793 | 8.57/8.81 |
| 7 | —$[CH_2-CH_2O]_2$—$CH_2CH_2$— | $R_1 = R_2 = R_3 = R_4 =$<br>n-$C_{12}H_{25}$ | 100 | 1.417 | | i - denotes isomer mixture

EXAMPLE 8

Bisneopentyl Glycol Dihydroxymethyltricyclo[5,2,1.0$^{2.6}$] decyl phosphite

A reaction apparatus prepared according to Example 1 is charged with 49.08 g (0.25 mol) of 3(4),8(9)-dihydroxymethyltricyclo[5.2,1.0$^{2.6}$]decane and 55.62 g (0.55 mol) of triethyl amine together with 250 ml of tetrahydrofuran (THF) and then, with stirring, 84.29 g (0.50 mol) of 2-chloro-5,5-dimethyl[1,3]dioxaphosphorinane in 100 ml of THF are added dropwise, with cooling, over 30 minutes.

The temperature is kept at 35° C. After stirring the mixture for 2 hours at 60° C. and then cooling it to room temperature, the precipitated triethyl amine hydrochloride is filtered off.

The solvent is evaporated by distillation on a rotary evaporator, the residue is distilled up to 60° C. and 0.1 mbar and, after addition of 1 g of filter aid (celite), clarified by filtration. 98.3 g of a colourless liquid are obtained, the structure and analytical values of which are given in the following Table 2 under Example 8.

Repeating the above procedure, but using the corresponding diols and chlorophosphorinanes gives the phosphites indicated in Table 2, Examples 9–16.

TABLE 2 phosphite: 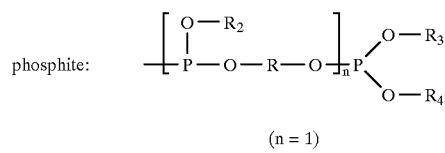

(n = 1)

| Example | R | R₁, R₂, R₃, R₄ | yield % of theory | $n_D^{20}$ | % P calcd./found |
|---|---|---|---|---|---|
| 8 | —CH₂—[tricyclodecane]—CH₂— | R₁ + R₂ = R₃ + R₄ = neopentyl (CH₃)₂C(CH₂—)(CH₂—) | 85 | 1.5045 | 13.45/13.38 |
| 9 | —[CH(CH₃)—CH₂]₂O— | R₁ + R₂ = R₃ + R₄ = neopentyl (CH₃)₂C(CH₂—)(CH₂—) | 83 | 1.4698 | 15.55/15.12 | phosphite: (same structure as above)

(n = 1)

| Example | R | R₁, R₂, R₃, R₄ | yield % of theory | $n_D^{20}$/m.p. | % P calcd./found |
|---|---|---|---|---|---|
| 10 | —[CH(CH₃)—CH₂]₂O— | R₁ + R₂ = R₃ + R₄ = —CH₂—CH₂— 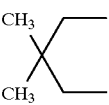 | 97 | 1.4770 | 19.72/19.53 |
| 11 | isosorbide (dimethyl bicyclic diether) | R₁ + R₂ = R₃ + R₄ = neopentyl (CH₃)₂C(CH₂—)(CH₂—) | 97 | m.p. 56–58° C. | 15.10/15.08 |

TABLE 2-continued

| Example | R | | R₁, R₂, R₃, R₄ | yield % of theory | m.p. / $n_D^{20}$ | % P calcd./found |
|---|---|---|---|---|---|---|
| 12 | 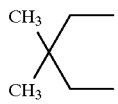 | | $R_1 + R_2 = R_3 + R_4 =$ ![CH3/CH3] | 93 | m.p.133–140° C. | 16.29/16.39 |
| 13 | —CH₂—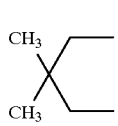—CH₂— | | $R_1 + R_2 = R_3 + R_4 =$ ![CH3/CH3] | 95 | m.p. 85–89° C. | 15.17/14.98 | phosphite: 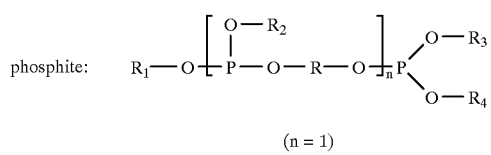

(n = 1)

| Example | R | R₁, R₂, R₃, R₄ | yield % of theory | $n_D^{20}$ | % P calcd./found |
|---|---|---|---|---|---|
| 14 | ─[CH₂CH₂]₂O | $R_1 + R_2 = R_3 + R_4 =$ CH₃\\CH₃ | 86 | 1.4775 | 16.73/16.15 |
| 15 | ─[CH₂CH₂─O─CH₂]₂ | $R_1 + R_2 = R_3 + R_4 =$ CH₃\\CH₃ | 87 | 1.4773 | 14.95/14.38 |
| 16 | ─[CH─CH₃]₂O<br>  │<br>  CH₃ | $R_1 + R_2 = R_3 + R_4 =$ H₃C\\H₉C₄ | | | |

Repeating the procedure of Example 1 or 8, the phosphites indicated in the following Tables 3 to 8 may be obtained.

TABLE 3
phosphite: $R_1-O\left[-P\begin{smallmatrix}O-R_2\\|\\\end{smallmatrix}-O-R-O\right]_n P\begin{smallmatrix}O-R_3\\\\O-R_4\end{smallmatrix}$
(n = 1)
| Example | R | $R_1, R_2, R_3, R_4$ |
|---|---|---|
| 17 | 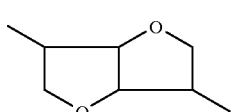 | $R_1 + R_2 = R_3 + R_4 =$ 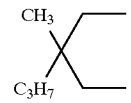 |
| 18 | 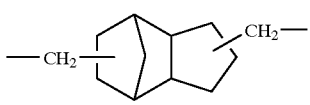 | $R_1 + R_2 = R_3 + R_4 =$ 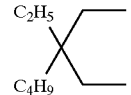 |
| 19 | $-[CH_2CH_2-O-CH_2]_2$ | $R_1 + R_2 = R_3 + R_4 =$ 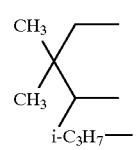 |
| 20 | $-[CH_2CH_2-O-CH_2]_2$ | $R_1 + R_2 = R_3 + R_4 =$  |
| 21 | 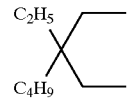 | $R_1 + R_2 = R_3 + R_4 =$ 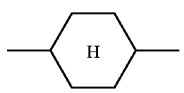 |
| 22 | 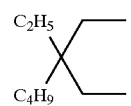 | $R_{1+R2} = R_3 + R_4 =$ |

TABLE 3-continued phosphite: $R_1-O-\left[\overset{\overset{O-R_2}{|}}{\underset{|}{P}}-O-R-O-\right]_n P\overset{O-R_3}{\underset{O-R_4}{\diagdown}}$ (n = 1)

| Example | R | $R_1, R_2, R_3, R_4$ |
|---|---|---|
| 23 | —CH$_2$—⟨H⟩—CH$_2$— | $R_1 + R_2 = R_3 + R_4 =$ <br><br> $\underset{C_4H_9}{\overset{C_2H_5}{\diagup}}\!\!\!\!\bigtimes$ |
| 24 | —CH$_2$—⟨H⟩—CH$_2$— | $R_1 = R_2 = R_3 = R_4 =$ <br><br> $C_4H_9\!-\!\underset{\underset{C_2H_5}{\mid}}{CH}\!-\!CH_2\!-$ |
| 25 | —CH$_2$—⟨H⟩—CH$_2$— | $R_1 = R_2 =$   $R_3 = R_4 =$ <br><br> $C_8H_{17}\!-\!\underset{\underset{C_6H_{13}}{\mid}}{CH}\!-\!CH_2$   $C_6H_{13}\!-\!\underset{\underset{C_4H_9}{\mid}}{CH}\!-\!CH_2\!-$ |
| 26 | —CH$_2$—⟨H⟩—CH$_2$— | $R_1 = R_2 =$   $R_3 + R_4 =$ <br> $C_{13/15}H_{27/31}-$ <br><br> $\underset{C_4H_9}{\overset{C_2H_5}{\diagup}}\!\!\!\!\bigtimes$ |

TABLE 4 phosphite: $R_1-O-\left[\overset{\overset{O-R_2}{|}}{\underset{|}{P}}-O-R-O-\right]_n P\overset{O-R_3}{\underset{O-R_4}{\diagdown}}$ (n = 2)

| Example | R | $R_1, R_2, R_3, R_4$ |
|---|---|---|
| 27 | 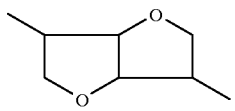 | $R_1 = R_2 = R_3 = R_4 =$ |

TABLE 4-continued phosphite:  $R_1-O-\left[\underset{\underset{O-R_2}{|}}{P}-O-R-O\right]_n P\underset{O-R_4}{\overset{O-R_3}{\diagup}}$ (n = 2)

| Example | R | $R_1, R_2, R_3, R_4$ | | |
|---|---|---|---|---|
| 28 | $-[CH_2CH_2-O-CH_2]_2$ | $R_1 = R_2 = R_3 = R_4 =$ n-$C_8H_{17}-$ | $C_8H_{17}-CH-CH_2$ <br>           $\|$ <br>           $C_6H_{13}$ | |
| 29 | $-[CH_2CH_2-O-CH_2]_2$ | $R_1 =$ $C_{12}H_{25}-$ | $R_2 =$ $C_{13}H_{27}-$ | $R_3 + R_4 =$ $\underset{C_4H_9}{\overset{C_2H_5}{\diagup}}\!\!\!\!\diagdown$ |
| 30 | $-[CH-CH_2]_2O$ <br>    $\|$ <br>    $CH_3$ | $R_1 = R_2 = R_3 = R_4 =$ i-$C_{10}H_{21}$ | $n_D^{20} = 1.4589$ | |
| 31 | $-[CH-CH_2]_2O$ <br>    $\|$ <br>    $CH_3$ | $R_1 = R_2 = R_3 = R_4 =$ $C_{13}H_{27}/C_{15}H_{31}$ | $n_D^° = 1.4594$ | |

TABLE 5 phosphite:  $R_1-O-\left[\underset{\underset{O-R_2}{|}}{P}-O-R-O\right]_n P\underset{O-R_4}{\overset{O-R_3}{\diagup}}$ (n = 3)

| Example | R | $R_1, R_2, R_3, R_4$ | |
|---|---|---|---|
| 32 | $-[CH-CH_2]_2O$ <br>    $\|$ <br>    $CH_3$ | $R_1 = R_2 =$ i-$C_8H_{17}-$ | $R_3 + R_4 =$ $\underset{C_4H_9}{\overset{C_2H_5}{\diagup}}\!\!\!\!\diagdown$ |
| 33 | $-[CH-CH_2]_2O$ <br>    $\|$ <br>    $CH_3$ | $R_1 = R_2 =$ <br> $C_6H_{13}-CH-CH_2-$ <br>          $\|$ <br>          $C_4H_9$ | $R_3 + R_4 =$ $\underset{C_4H_9}{\overset{C_2H_5}{\diagup}}\!\!\!\!\diagdown$ |

TABLE 5-continued phosphite: $R_1-O-\left[\underset{\underset{O-R_2}{|}}{P}-O-R-O\right]_n P\underset{O-R_4}{\overset{O-R_3}{<}}$ (n = 3)

| Example | R | $R_1, R_2, R_3, R_4$ | |
|---|---|---|---|
| 34 | ―⟨H⟩― | $R_1 = R_2 = R_3 = R_4 =$<br><br>$C_8H_{17}-\underset{\underset{C_6H_{13}}{|}}{CH}-CH_2$ | |
| 35 | ―[CH―CH$_2$]$_2$O<br>      \|<br>      CH$_3$ | $R_1 = R_2 = R_3 = R4 =$<br>i-C$_{10}$H$_{21}$ | $n_D^{20} = 1.4595$ |
| 36 | ―CH$_2$―⟨H⟩―CH$_2$― | $R_1 + R_2 = R_3 + R_4 =$<br><br>$C_2H_5$<br>  \\<br>   X<br>  /<br>$C_4H_9$ | |

TABLE 6 phosphite: $R_1-O-\left[\underset{\underset{O-R_2}{|}}{P}-O-R-O\right]_n P\underset{O-R_4}{\overset{O-R_3}{<}}$ (n = 4)

| Example | R | $R_1, R_2, R_3, R_4$ |
|---|---|---|
| 37 | ―[CH$_2$―CH$_2$]$_2$O | $R_1, R_2, R_3, R_4 =$<br><br>i-C$_{18}$H$_{37}$/<br><br>⟨⟩―CH$_2$CH$_2$―<br><br>at a molecular ratio of 2:4 |

TABLE 7 phosphite: $R_1-O-\left[\underset{\underset{O-R_2}{|}}{P}-O-R-O\right]_n P\underset{O-R_4}{\overset{O-R_3}{\diagup}}$ (n = 5)

| Example | R | $R_1, R_2, R_3, R_4$ |
|---|---|---|
| 38 | $-[CH-CH_2]_2O$<br>$\quad\ \|$<br>$\quad CH_3$ | $R_1 + R_2 = R_3 + R_4 =$ 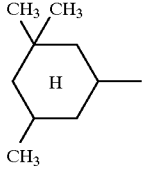 |
| 39 | $-[CH-CH_2]_2O$<br>$\quad\ \|$<br>$\quad CH_3$ | $R_1 = R_2 = R_3 = R_4 = \quad n_D^{20} = 1.4607$<br>i-$C_{10}H_{21}$ |
| 40 | $-[CH_2CH_2O]_2CH_2CH_2-$ | $R_1, R_2, R_3, R_4 =$<br>2-butyloctyl/n-dodecyl at a molar<br>ratio of 3:4 |

TABLE 8 phosphite: $R_1-O-\left[\underset{\underset{O-R_2}{|}}{P}-O-R-O\right]_n P\underset{O-R_4}{\overset{O-R_3}{\diagup}}$ (n = 6)

| Example | R | $R_1, R_2, R_3, R_4$ |
|---|---|---|
| 41 | $-[CH_2-CH_2]_2O$ | $R_1 = \quad R_2 = \quad R_3 + R_4 =$<br>$C_{12}H_{25}-C_{13}H_{27}-$ 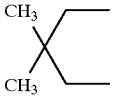 |
| 42 | $-[CH-CH_2]_2O$<br>$\quad\ \|$<br>$\quad CH_3$ | $R_1 = R_2 = R_3 = R_4 = n_D^{20} = 1.4604$<br>i-$C_{10}H_{21}$ |
| 43 | $-CH_2-\text{(tricyclodecane)}-CH_2-$ | $R_1 = R_2 = R_3 = R_4 =$<br>i-$C_8H_{17}$ |

EXAMPLE 44

100 Parts of S-PVC (K value 65-71), 20 parts of dioctyl phthalate and 2 parts of a barium/zinc stabiliser comprising barium-2-ethylhexanoate, barium-p-tert-butylbenzoate, zinc oleate and basic barium nonylphenolate, and 23.6% of a novel phosphite (corresponding to 0.5 part, based on 100 parts of PVC) according to Table 8, are plasticised at 190° C. on a mixer roll for 5 minutes and the resulting film (0.3 mm) is then subjected to thermomechanical stress in a continuous rolling test until the onset of an strong dark discoloration (termination time). At intervals of 5 minutes each, samples are taken to measure the degree of discolouration (yellowness index YI). The effectivity of the stabiliser system is determined by measuring the YI values in accordance with ASTM D 1925-70 at 5 and 30 minutes and measuring the termination time (see Table 9).

TABLE 9

Continuous rolling test
Yellowness index YI; thermostability (termination time)

| Phosphite acc. to Example | YI 5 [min] | 30 [min] | Thermostability termination time [min] |
|---|---|---|---|
| 2 | 4.7 | 12.1 | 68 |
| 8 | 5.2 | 12.2 | 69 |
| 14 | 4.9 | 10.1 | 70 |
| 15 | 4.9 | 9.8 | 74 |

The lower the YI value, the more effectively does the stabiliser system prevent yellowing and damage of the organic polymeric material. The time to the start of a substantial discolouration (termination time) indicates the long-term stability.

A stabliliser effective, the longer the discolouration is delayed under thermal stress.

EXAMPLE 45

A mixture consisting of 100 parts of E+S-PVC mixture (K value 80), 50.1 parts of plasticiser mixture consisting of dibutyl phthalate and dioctyl phthalate, 3.7 parts of an epoxidised fatty acid ester, 1.1 parts of a butyltin mercaptopropionate stabiliser (main component: dibutyltin isooctylmercaptopropionate) and 1.6 parts of a novel phosphite are processed to a plastisol and then gelled on a PVC flooring substrate at 200° C. to a 0.5 mm film which is tested for discolouration at 100° C. in a static heat test. To this purpose, the yellowness index in accordance with ASTM D 1925-70 is measured at specific intervals. The results are presented in the following Table 10.

TABLE 10

Static heat test at 200° C.
Yellowness index YI

| Phosphite acc. to Example | Test time [min] | | | | | |
|---|---|---|---|---|---|---|
| | 0 | 5 | 7 | 9 | 11 | 13 |
| 2 | 20.1 | 13.9 | 16.8 | 22.7 | 29.5 | 49.8 |
| — | 37 | 43 | 53 | 58 | 64 | 68 |

EXAMPLE 46

A mixture consisting of 100 parts of S-PVC (K value 68), 3 parts of chalk (®OMYALITE 95T), 0.6 part of calcium stearate, 2.7 parts of a stabiliser consisting of an epoxy resin, NaClO$_4$.H$_2$O (mounted on a substrate consisting of chalk/calcium silicate), a hydrocarbon wax and 1,3-dimethyl-6-aminouracil and 0.4 part of a novel phosphite is plasticised on a mixer roll for 5 minutes at 190° C. Test strips of the resulting 0.3 mm film are subjected to thermal stress in a Mathis® Thermo-Takter for 40 minutes at 190° C. The yellowness index (YI) is then measured in accordance with ASTM D 1925-70. The results are presented in Table 11.

TABLE 11

Static heat test at 190° C.
Yellowness index YI

| Phosphite acc. to Example | Test time [min] | | | | | | |
|---|---|---|---|---|---|---|---|
| | 0 | 5 | 10 | 15 | 20 | 30 | 40 |
| 2 | 19.1 | 21.7 | 22.9 | 26.8 | 32.3 | 55.3 | 97.1 |

EXAMPLE 47

A mixture consisting of 100 parts of S-PVC (K value 60), 18 parts of dioctyl phthalate as plasticiser, 2 parts of epoxidised fatty acid ester, 0.8 part of a novel phosphite and 1.5 parts of a calcium/zinc stearate (~3/2) mixture are plasticised in a mixer roll over 5 minutes at 190° C. Test strips of the resulting 0.3 mill rolled sheet are subjected to a static heat test in a Mathis ®Thermo-Takter at 180° C., and after 6 minutes the yellowness index (YI) is measured in accordance with ASTM D 1925-70 (initial colour). The results are presented in Table 12.

TABLE 12

Static heat test at 180° C.
Yellowness index YI

| Phosphite acc. to Example | Initial colour YI [6 min] |
|---|---|
| — | 27.9 |
| 2 | 12.2 |
| 15 | 6.7 |

What is claimed is:
1. A composition, comprising
(i) a halogen-containing polymeric material, and
(ii) at least one phosphite of formula I

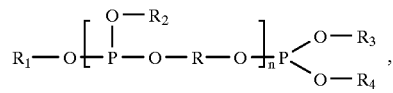

wherein
n is a number from 1 to 6,
R is a divalent linking group of formulae

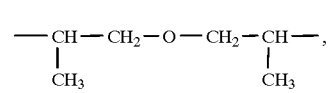

(BR1)

(BR2)

-continued

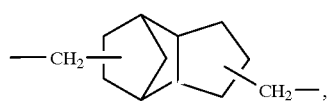 (BR3)

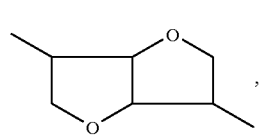 (BR4)

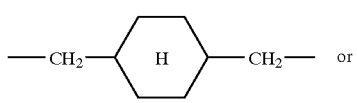 (BR5)

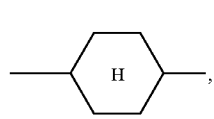 (BR6)

m is a number from 1 to 5, $R_1$, $R_2$, $R_3$ and $R_4$ are each independently of one another $C_4$–$C_{22}$ alkyl, $C_7$–$C_9$ phenylalkyl, $C_5$–$C_8$ cycloalkyl or $C_1$–$C_4$ alkyl-$C_5$–$C_8$ cycloalkyl, or $R_1$ and $R_2$ and/or $R_3$ and $R_4$ together are $C_2$–$C_9$ alkylene or a group of formula

with the provisos that
a) the composition does not contain any Ba-, Zn- and/or Ca-stabilisers, if $R_1$+$R_2$ and $R_3$+$R_4$ are a group of formula

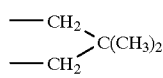

and if R is BR1 or BR2, and
b) m is different from 2, if $R_1$, $R_2$, $R_3$ and $R_4$ are identical and are $C_{12}$–$C_{22}$ alkyl and if R is BR2; and at least one component (iii) which is an organotin compound selected from organotin sulfides, organotin mercaptides or organotin mercaptocarboxylates.

2. A composition according to claim 1, wherein component (i) is a vinyl chloride homo- or copolymer.

3. A composition according to claim 1, wherein n is 1 to 4.

4. A composition according to claim 3, wherein n is 1 to 3.

5. A composition according to claim 3, wherein n is 1.

6. A composition according to claim 1, wherein $R_1$, $R_2$, $R_3$ and $R_4$ are each independently of one another $C_6$–$C_{22}$alkyl or $C_7$–$C_9$phenylalkyl, or $R_1$ and $R_2$ and/or $R_3$ and $R_4$ together are $C_2$–$C_9$alkylene.

7. A composition according to claim 6, wherein m is 1 or 2, and $R_1$, $R_2$, $R_3$ and $R_4$ are each independently of one another $C_6$–$C_{15}$alkyl, $C_7$–$C_9$phenylalkyl, or $R_1$ and $R_2$ and/or $R_3$ and $R_4$ together are $C_2$–$C_9$alkylene.

8. A composition according to claim 1, wherein R is a divalent linking group of formula BR1, BR3 or BR4.

9. A composition according to claim 1, wherein R is a divalent linking group of formula BR1, BR2 or BR3.

10. A composition according to claim 1, wherein R is a divalent linking group of formula BR1.

11. A composition according to claim 10, wherein $R_1$, $R_2$, $R_3$ and $R_4$ are each independently of one another $C_6$–$C_{15}$alkyl or $C_7$–$C_8$phenylalkyl.

12. A composition according to claim 1, wherein $R_1$, $R_2$, $R_3$ and $R_4$ are identical.

13. A composition according to claim 1, wherein $R_1$+$R_2$ and $R_3$+$R_4$ are identical.

14. A composition according to claim 10, wherein $R_1$, $R_2$, $R_3$ and $R_4$ are $C_6$–$C_{11}$alkyl, $C_7$–$C_8$-phenylalkyl or $C_5$–$C_8$cycloalkyl, or $R_1$ and $R_2$ and/or $R_3$ and $R_4$ together are $C_2$–$C_9$alkylene.

15. A composition according to claim 1, wherein $R_1$, $R_2$, $R_3$ and $R_4$ are $C_6$–$C_{22}$alkyl, $C_7$–$C_9$phenylalkyl or $C_5$–$C_8$cycloalkyl.

16. A composition according to claim 1, comprising the phosphite of formula I in an amount of 0.01–10% by weight, based on component (i).

17. A composition according to claim 1, wherein component (iii) is a lubricant, plasticiser, pigment, antiblocking agent, modifier, processing assistant, blowing agent, antistatic agent, biocide, antifogging agent, colourant, flame retardant, filler, antioxidant, light stabiliser and/or another processing stabiliser.

18. A process for stabilising halogen-containing polymeric materials, which comprises incorporating therein at least one composition of as defined in claim 1.

19. A process according to claim 18, wherein the polymeric material is a polyvinyl chloride.

20. A phosphite of formula I

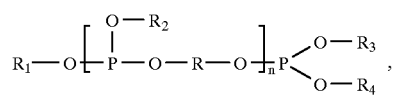 (I)

wherein n is a number from 1 to 6,

R is a divalent linking group of formulae

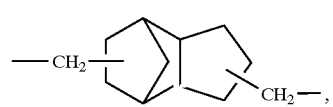 (BR3)

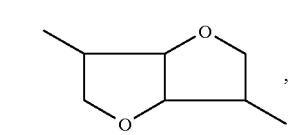 (BR4)

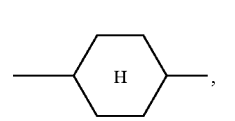 (BR6)

$R_1$, $R_2$, $R_3$ and $R_4$ are each independently of one another $C_4$–$C_{22}$ alkyl, $C_7$–$C_9$ phenylalkyl, $C_5$–$C_8$ cycloalkyl or $C_1$–$C_4$ alkyl, -$C_5$–$C_5$ cycloalkyl, or $R_1$ and $R_2$ and/or $R_3$ and $R_4$ together are $C_2$–$C_9$ alkylene or a group of formula

21. A phosphite according to claim 20, wherein $R_1$, $R_2$, $R_3$ and $R_4$ or $R_1+R_2$ and $R_3+R_4$ are each identical.

22. A phosphite according to claim 20, wherein n is 1 to 4.

23. A phosphite according to claim 20, wherein n is 1.

24. A phosphite according to claim 20, wherein $R_1$, $R_2$, $R_3$ and $R_4$ are $C_8$–$C_{18}$alkyl, or $R_1$ and $R_2$ and/or $R_3$ and $R_4$ together are $C_2$–$C_9$alkylene.

25. A composition comprising a synthetic or semi-synthetic organic polymer and at least one phosphite as defined in claim 20.

26. A composition according to claim 25, wherein the polymer is a polyolefin, polyurethane, polycarbonate, polyamide or elastomer.

27. A composition comprising a lubricant, a hydraulic fluid or metal processing fluid and at least one phosphite as defined in claim 20.

28. A composition according to claim 26, additionally comprising one or more further stabilisers.

29. A composition according to claim 28, further comprising one or more antioxidants or light stabilisers.

30. A process for stabilising synthetic or semi-synthetic organic polymers, which comprises incorporating therein at least one phosphite as defined in claim 20.

31. A process for enhancing the performance properties of lubricants, hydraulic fluids or metal processing fluids, which comprises adding thereto at least one phosphite as defined in claim 20.

32. A phosphite of formula I

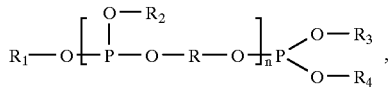
(I)

wherein n is number from 2 to 6,

R is a divalent linking group of formulae

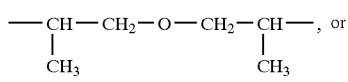
(BR1)

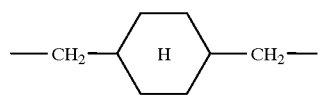
(BR5)

m is a number from 1 to 5, $R_1$, $R_2$, $R_3$ and $R_4$ are each independently of one another $C_4$–$C_{22}$ alkyl, $C_7$–$C_9$ phenylalkyl, $C_5$–$C_8$ cycloalkyl or $C_1$–$C_4$ alkyl -$C_5$–$C_5$ cycloalkyl, or $R_1$ and $R_2$ and/or $R_3$ and $R_4$ together are $C_2$–$C_9$ alkylene or a group of formula

33. A phosphite according to claim 32, wherein n is 2 to 5.

34. A phosphite according to claim 32, wherein $R_1$, $R_2$, $R_3$ and $R_4$ are $C_8$–$C_{18}$alkyl, or $R_1$ and $R_2$ and/or $R_3$ and $R_4$ together are $C_2$–$C_9$alkylene.

35. A composition comprising a synthetic or semi-synthetic organic polymer and at least one phosphite as defined in claim 32.

36. A composition according to claim 35, wherein the polymer is a polyolefin, polyurethane, polycarbonate, polyamide or elastomer.

37. A composition comprising a lubricant, a hydraulic fluid or metal processing fluid and at least one phosphite as defined in claim 32.

38. A composition according to claim 35, additionally comprising one or more further stabilisers.

39. A composition according to claim 38, further comprising one or more antioxidants or light stabilisers.

40. A process for stabilising synthetic or semi-synthetic organic polymers, which comprises incorporating therein at least one phosphite as defined in claim 32.

41. A composition comprising a lubricant, a hydraulic fluid or metal processing fluid and at least one phosphite of formula I

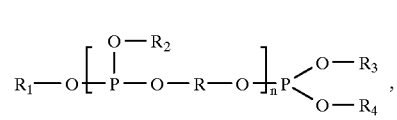
(I)

wherein n is a number from 1 to 6,

R is a divalent linking group of formulae

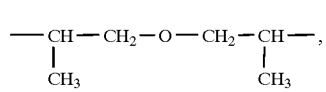
(BR1)

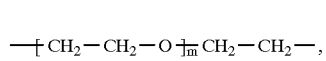
(BR2)

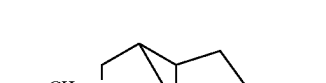
(BR3)

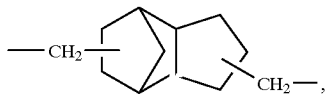
(BR4)

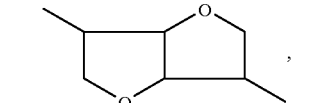

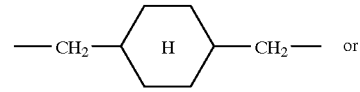
(BR5)

-continued

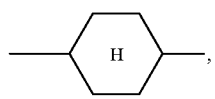
(BR6)

m is a number from 1 to 5,

R$_1$, R$_2$, R$_3$ and R$_4$ are each independently of one another C$_4$–C$_{22}$ alkyl, C$_7$–C$_9$ phenylalkyl, C$_5$–C$_8$ cycloalkyl or C$_1$–C$_4$ alkyl -C$_5$–C$_5$ cycloalkyl, or R$_1$ and R$_2$ and/or R$_3$ and R$_4$ together are C$_2$–C$_9$ alkylene or a group of formula

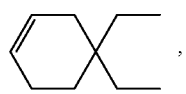

with the proviso the
a) the composition does not contain any Ba-, Zn- and/or Ca-stabilizers, if R$_1$+R$_2$ and R$_3$+R$_4$ are a group of formula

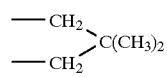

and if R is BR1 or BR2, and
b) m is different from 2, if R$_1$, R$_2$, R$_3$ and R$_4$ are identical and are C$_{12}$–C$_{22}$ alkyl and if R is BR2.

42. A process for enhancing the performance properties of lubricants, hydraulic fluids or metal processing fluids, which comprises adding thereto at least one phosphite of formula I

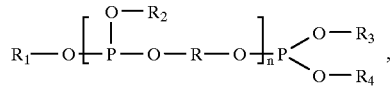
(I)

wherein
n is a number from 1 to 6,
R is a divalent linking group of formulae

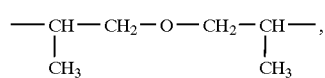
(BR1)

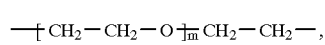
(BR2)

-continued

(BR3)

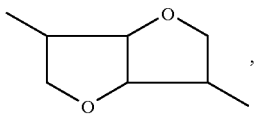
(BR4)

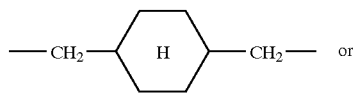 or
(BR5)

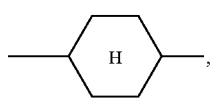
(BR6)

m is a number from 1 to 5,

R$_1$, R$_2$, R$_3$ and R$_4$ are each independently of one another C$_4$–C$_{22}$ alkyl, C$_7$–C$_9$ phenylalkyl, C$_5$–C$_8$ cycloalkyl or C$_1$–C$_4$ alkyl -C$_5$–C$_5$ cycloalkyl, or R$_1$ and R$_2$ and/or R$_3$ and R$_4$ together are C$_2$–C$_9$ alkylene or a group of formula

with the provisos that
a) the composition does not contain any Ba-, Zn- and/or Ca-stabilisers, if R$_1$+R$_2$ and R$_3$+R$_4$ are a group of formula

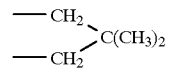

and if R is BR1 or BR2, and
b) m is different from 2, if R$_1$, R$_2$, R$_3$ and R$_4$ are identical and are C$_{12}$–C$_{22}$ alkyl and if R is BR2.

43. A process for enhancing the performance properties of lubricants, hydraulic fluids or metal processing fluids, which comprises adding thereto at least one phosphite as defined in claim 32.

* * * * *